United States Patent
Bowen et al.

(10) Patent No.: US 11,312,752 B2
(45) Date of Patent: Apr. 26, 2022

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Arlene R. Howe, Clarkson Valley, MO (US); Uma Kesanapalli, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/810,810

(22) Filed: Mar. 5, 2020

(65) Prior Publication Data

US 2020/0262876 A1 Aug. 20, 2020

Related U.S. Application Data

(62) Division of application No. 15/727,883, filed on Oct. 9, 2017, now Pat. No. 10,626,151.

(60) Provisional application No. 62/406,082, filed on Oct. 10, 2016.

(51) Int. Cl.
*C07K 14/32* (2006.01)
*C12N 15/82* (2006.01)
*C07K 14/325* (2006.01)
*C12Q 1/6895* (2018.01)

(52) U.S. Cl.
CPC ........ *C07K 14/325* (2013.01); *C12N 15/8286* (2013.01); *C12Q 1/6895* (2013.01)

(58) Field of Classification Search
None
See application file for complete search history.

(56) References Cited

U.S. PATENT DOCUMENTS

| | | |
|---|---|---|
| 6,204,246 B1 | 3/2001 | Bosch et al. |
| 6,780,408 B1 | 8/2004 | Bosch et al. |
| 9,499,835 B2 | 11/2016 | Meade et al. |
| 9,556,453 B2 | 1/2017 | Meade et al. |
| 9,567,602 B2 | 2/2017 | Meade et al. |
| 9,663,795 B2 | 5/2017 | Meade et al. |
| 9,796,982 B2 | 10/2017 | Meade et al. |
| 2003/0195336 A1 | 10/2003 | Baum et al. |
| 2004/0197916 A1 | 10/2004 | Carozzi et al. |
| 2004/0221334 A1 | 11/2004 | Baum et al. |
| 2008/0040827 A1* | 2/2008 | Donovan ............. C07K 14/325 800/302 |
| 2009/0036377 A1 | 2/2009 | Carozzi et al. |

OTHER PUBLICATIONS

Honee et al., "Nucleotide sequence of crystal protein gene isolated from *B. thuringiensis* subspecies *entomocidus* 60.5 coding for a toxin highly active against *Spodoptera* species," *Nucleic Acids Res*, 16:6240, 1988.

Kao et al., "Cloning and expression of the insecticidal crystal protein gene Cry1Ca9 of *Bacillus thuringiensis* G10-01A from Taiwan granaries," *Curr Microbiol*, 47:295-299, 2003.

Palma et al., "*Bacillus thuringiensis* toxins: An overview of their biocidal activity," *Toxins*, 6:3296-3325, 2014.

Sanchis et al., "Nucleotide sequence and analysis of the N-terminal coding region of the *Spodoptera*-active delta-endotoxin gene of *Bacillus thuringiensis aizawai* 7.29," *Mol Microbiol*, 3:229-238, 1989.

Smith et al., "Mosquitocidal activity of the CryIC d-endotoxin from *Bacillus thuringiensis* subsp. *aizawai*," *Appl Environ Microbiol*, 62:680-684, 1996.

Visser et al., "Genes from *Bacillus thuringiensis entomocidus* 60.5 coding for insect-specific crystal proteins," *Mol Gen Genet*, 212:219-224, 1988.

International Search Report and Written Opinion regarding International Application No. PCT/US2017/055731, dated Feb. 9, 2018.

* cited by examiner

*Primary Examiner* — Matthew R Keogh
(74) *Attorney, Agent, or Firm* — Dentons US LLP; Timothy Ball

(57) ABSTRACT

Pesticidal proteins exhibiting toxic activity against Lepidopteran pest species are disclosed, and include, but are not limited to, TIC4472, TIC4472PL, TIC1425, TIC2613, and TIC2613PL. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding the pesticidal proteins of the present invention. Methods for detecting the presence of the recombinant nucleic acid sequences or the proteins of the present invention in a biological sample, and methods of controlling Lepidopteran species pests using any of the TIC4472, TIC4472PL, TIC1425, TIC2613, and TIC2613PL pesticidal proteins are also provided.

32 Claims, No Drawings

Specification includes a Sequence Listing.

INSECT INHIBITORY PROTEINS

REFERENCE TO RELATED APPLICATION

This application is a divisional of U.S. application Ser. No. 15/727,883, filed Oct. 9, 2017, which application claims the benefit of U.S. provisional application No. 62/406,082, filed Oct. 10, 2016, each of which is herein incorporated by reference in its entirety.

INCORPORATION OF SEQUENCE LISTING

The file named "MONS426US_ST25.txt" containing a computer-readable form of the Sequence Listing was created on Oct. 8, 2017. This file is 77,030 bytes (measured in MS-Windows®), filed contemporaneously by electronic submission (using the United States Patent Office EFS-Web filing system), and incorporated herein by reference in its entirety.

FIELD OF THE INVENTION

The invention generally relates to the field of insect inhibitory proteins. A novel class of proteins exhibiting insect inhibitory activity against agriculturally-relevant pests of crop plants and seeds are disclosed. In particular, the disclosed class of proteins is insecticidally active against agriculturally-relevant pests of crop plants and seeds, particularly Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, Beet armyworm (*Spodoptera exigua*), Corn earworm (*Helicoverpa zea*), Cotton leaf worm (*Alabama argillacea*), European corn borer (*Ostrinia nubilalis*), Fall armyworm (*Spodoptera frugiperda*), Old World bollworm (*Helicoverpa armigera*), Oriental leaf worm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus*, *Lysinibacillus sphaericus* ("Ls" formerly known as *Bacillus sphaericus*) and *Paenibacillus popilliae*.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors disclose herein a novel protein toxin family from *Bacillus thuringiensis*, along with similar toxin proteins, variant proteins, and exemplary recombinant proteins that exhibit insecticidal activity against target Lepidopteran species, particularly against Beet armyworm (*Spodoptera exigua*), Corn earworm (*Helicoverpa zea*), Cotton leaf worm (*Alabama argillacea*), European corn borer (*Ostrinia nubilalis*), Fall armyworm (*Spodoptera frugiperda*), Old World bollworm (*Helicoverpa armigera*), Oriental leaf worm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*).

SUMMARY OF THE INVENTION

Disclosed herein is a novel group of pesticidal proteins with insect inhibitory activity (toxin proteins), referred to herein as TIC4472, TIC1425, and TIC2613 belonging to the TIC4472 protein toxin class, which are shown to exhibit inhibitory activity against one or more pests of crop plants. The TIC4472 protein and proteins in the TIC4472 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter fragment operably linked to a polynucleotide segment encoding a pesticidal protein or fragment thereof, wherein (a) said pesticidal protein comprises the amino acid sequence of SEQ ID NO:4, SEQ ID NO:2, or SEQ ID NO:6; or (b) said pesticidal protein comprises an amino acid sequence having: (i) at least 93%, or 95%, or 98%, or 99%, or about 100% amino acid sequence identity to SEQ ID NO:4, SEQ ID NO:2, or SEQ ID NO:6; or (ii) at least 73%, or 75%, or 80%, or 85%, or 90%, or 95%, or about 100% amino acid sequence identity to SEQ ID NO:8 or SEQ ID NO:10; or (c) said polynucleotide segment hybridizes to a polynucleotide having the nucleotide sequence of SEQ ID NO:3, SEQ ID NO:1, SEQ ID NO:5, SEQ ID NO:7, or SEQ ID NO:9; or (d) said polynucleotide segment encoding a pesticidal protein or fragment thereof comprises a polynucleotide sequence having at least 65%, or 70%, or 75%, or 80%, or 85%, or 90%, or 95%, or 98%, or 99%, or about 100% sequence identity to the nucleotide sequence of SEQ ID NO:3, SEQ ID NO:1, SEQ ID NO:5, SEQ ID NO:7, or SEQ ID NO:9; or (e) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application, host cells comprising a recombinant nucleic acid molecule of the application are provided, wherein the host cell is selected from the group consisting of a bacterial and a plant cell. Contemplated bacterial host cells include *Agrobacterium, Rhizobium, Bacillus, Brevibacillus, Escherichia, Pseudomonas, Klebsiella, Pantoec,* and *Erwinia*. In certain embodiments, said *Bacillus* species is *Bacillus cereus* or *Bacillus thuringiensis*, said *Brevibacillus* is *Brevibacillus laterosperous*, or *Escherichia* is *Escherichia coli*. Contemplated plant host cells include a dicotyledonous plant cell and a monocotyledonous plant cell. Contemplated plant cells further include an alfalfa, banana, barley, bean, broccoli, cabbage, brassica, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Lepidopteran insects, including Beet armyworm (*Spodoptera exigua*), Corn earworm (*Helicoverpa zea*), Cotton leaf worm (*Alabama argillacea*), European corn borer (*Ostrinia nubilalis*), Fall armyworm (*Spodoptera frugiperda*), Old World bollworm (*Helicoverpa armigera*), Oriental leaf worm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*).

Also contemplated in this application are plants comprising a recombinant nucleic acid molecule comprising a heterologous promoter fragment operably linked to a polynucleotide segment encoding a pesticidal protein or fragment thereof, wherein: (a) said pesticidal protein comprises the amino acid sequence of SEQ ID NO:4, SEQ ID NO:2, or SEQ ID NO:6; or (b) said pesticidal protein comprises an amino acid sequence having: (i) at least 93%, or 95%, or 98%, or 99%, or about 100% amino acid sequence identity to SEQ ID NO:4, SEQ ID NO:2, or SEQ ID NO:6; or (ii) at least 73%, or 75%, or 80%, or 85%, or 90%, or 95%, or about 100% amino acid sequence identity to SEQ ID NO:8 or SEQ ID NO:10; or (c) said polynucleotide segment hybridizes under stringent hybridization conditions to the compliment of the nucleotide sequence of SEQ ID NO:3 or SEQ ID NO:9; or (d) said plant exhibits a detectable amount of said pesticidal protein. In certain embodiments, the pesticidal protein comprises SEQ ID NO:4, SEQ ID NO:2, SEQ ID NO:6, SEQ ID NO:8, or SEQ ID NO:10. In one embodiment, the plant is either a dicotyledonous plant or a monocotyledonous plant. In another embodiment, the plant is further selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 and a DIG-11 protein.

Commodity products comprising a detectable amount of the recombinant nucleic acid molecules disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application are methods of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation, is provided wherein the cells of said plant comprise: (a) a recombinant nucleic acid molecule encoding an insecticidally effective amount of a pesticidal protein as set forth in SEQ ID NO:4, SEQ ID NO:2, or SEQ ID NO:6; or (b) an insecticidally effective amount of a protein comprising an amino acid sequence having: (i) at least 93%, or 95%, or about 100% amino acid sequence identity to SEQ ID NO:4, SEQ ID NO:2, or SEQ ID NO:6; or (ii) at least 73%, or 75%, or 80%, or 85%, or 90%, or 95%, or about 100% amino acid sequence identity to SEQ ID NO:8 or SEQ ID NO:10.

Also disclosed in this application are methods for controlling a Lepidopteran species pest, and controlling a Lepidopteran species pest infestation of a plant, particularly a crop plant. The method comprises, in one embodiment, (a) contacting the pest with an insecticidally effective amount of a pesticidal proteins as set forth in SEQ ID NO:4, SEQ ID NO:2, or SEQ ID NO:6; or (b) contacting the pest with an insecticidally effective amount of one or more pesticidal proteins comprising an amino acid sequence having: (i) at least 93%, or 95%, or about 100% amino acid sequence identity to identity to SEQ ID NO:4, SEQ ID NO:2, or SEQ ID NO:6; or (ii) least 73%, or 75%, or 80%, or 85%, or 90%, or 95%, or about 100% amino acid sequence identity to SEQ ID NO:8 or SEQ ID NO:10.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NO:4, SEQ ID NO:2, or SEQ ID NO:6; or (b) said pesticidal protein comprises an amino acid sequence having: (i) at least 93%, or 95%, or 98%, or 99%, or about 100% amino acid sequence identity to SEQ ID NO:4, SEQ ID NO:2, or SEQ ID NO:6; or (ii) at least 73%, or 75%, or 80%, or 85%, or 90%, or 95%, or about 100% amino acid sequence identity to SEQ ID NO:8 or SEQ ID NO:10; or (c) said polynucleotide segment hybridizes to a polynucleotide having the nucleotide sequence of SEQ ID NO:4, SEQ ID NO:2, SEQ ID NO:6, SEQ ID NO:8, or SEQ ID NO:10. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:3 or SEQ ID NO:9, or a sequence that encodes a pesticidal protein comprising an amino acid sequence having: (a) at least 93%, or 95%, or 98%, or 99%, or about 100% amino acid sequence identity to SEQ ID NO:4, SEQ ID NO:2, or SEQ ID NO:6; or (b) at least 73%, or 75%, or 80%, or 85%, or 90%, or 95%, or about 100% amino acid sequence identity to SEQ ID NO:8 or SEQ ID NO:10. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NO:4, SEQ ID NO:2, SEQ ID NO:6, SEQ ID NO:8, or SEQ ID NO:10; or said pesticidal protein comprises an amino acid sequence having: (a) at least 93%, or 95%, or 98%, or 99%, or about 100% amino acid sequence identity to SEQ ID NO:4, SEQ ID NO:2, or SEQ ID NO:6; or (b) at least 73%, or 75%, or 80%, or 85%, or 90%, or 95%, or about 100% amino acid sequence identity to SEQ ID NO:8 or SEQ ID NO:10. In one embodiment, the method comprises: (a) contacting a sample with an immunoreactive antibody; and (b) detecting the presence of the protein. In some embodiments the step of detecting comprises an ELISA, or a Western blot.

BRIEF DESCRIPTION OF THE SEQUENCES

SEQ ID NO:1 is a nucleic acid sequence encoding a TIC4472 pesticidal protein obtained from *Bacillus thuringiensis* species EG10742.

SEQ ID NO:2 is the amino acid sequence of the TIC4472 pesticidal protein.

SEQ ID NO:3 is a synthetic coding sequence encoding a TIC4472PL pesticidal protein designed for expression in a plant cell wherein an additional alanine codon is inserted immediately following the initiating methionine codon.

SEQ ID NO:4 is the amino acid sequence of TIC4472PL encoded by a synthetic coding sequence designed for expression in a plant cell (SEQ ID NO:3), and wherein an additional alanine amino acid is inserted immediately following the initiating methionine.

SEQ ID NO:5 is a nucleic acid sequence encoding a TIC1425 pesticidal protein obtained from *Bacillus thuringiensis* species EG10731.

SEQ ID NO:6 is the amino acid sequence of the TIC1425 pesticidal protein.

SEQ ID NO:7 is a nucleic acid sequence encoding a TIC2613 pesticidal protein obtained from *Bacillus thuringiensis* species EG5408.

SEQ ID NO:8 is the amino acid sequence of the TIC2613 pesticidal protein.

SEQ ID NO:9 is a synthetic coding sequence encoding a TIC2613PL pesticidal protein designed for expression in a plant cell wherein an additional alanine codon is inserted immediately following the initiating methionine codon.

SEQ ID NO:10 is the amino acid sequence of TIC2613PL encoded by a synthetic coding sequence designed for expression in a plant cell (SEQ ID NO:9), and wherein an additional alanine amino acid is inserted immediately following the initiating methionine.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC4472, TIC4472PL, TIC1425, TIC2613, and TIC2613PL are disclosed herein, and address each of these needs, particularly against a broad spectrum of Lepidopteran insect pests, and more particularly against Beet armyworm (*Spodoptera exigua*), Corn earworm (*Helicoverpa zea*), Cotton leafworm (*Alabama argillacea*), European corn borer (*Ostrinia nubilalis*), Fall armyworm (*Spodoptera frugiperda*), Old World bollworm (*Helicoverpa armigera*), Oriental leafworm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*).

Reference in this application to TIC4472, "TIC4472 protein", "TIC4472 protein toxin", "TIC4472 toxin protein", "TIC4472 pesticidal protein", "TIC4472-related toxins", "TIC4472-related toxin proteins", TIC4472PL, "TIC4472PL protein", "TIC4472PL protein toxin", "TIC4472PL toxin protein", "TIC4472PL pesticidal protein", "TIC4472PL-related toxins", "TIC4472PL-related toxin proteins", TIC1425, "TIC1425 protein", "TIC1425 protein toxin", "TIC1425 toxin protein", "TIC1425 pesticidal protein", "TIC1425-related toxins", "TIC1425-related toxin proteins", TIC2613, "TIC2613 protein", "TIC2613 protein toxin", "TIC2613 toxin protein", "TIC2613 pesticidal protein", "TIC2613-related toxins", "TIC2613-related toxin proteins", TIC2613PL, "TIC2613PL protein", "TIC2613PL protein toxin", "TIC2613PL toxin protein", "TIC2613PL pesticidal protein", "TIC2613PL-related toxins", "TIC2613PL-related toxin proteins", and the like, refer to any novel pesticidal protein or insect inhibitory protein, that comprises, that consists of, that is substantially homologous to, that is similar to, or that is derived from any pesticidal protein or insect inhibitory protein sequence of TIC4472 (SEQ ID NO:2), TIC4472PL (SEQ ID NO:4), TIC1425 (SEQ ID NO:6), TIC2613 (SEQ ID NO:8), or TIC2613PL (SEQ ID NO:10) and pesticidal or insect inhibitory segments thereof, or combinations thereof, that confer activity against Lepidopteran pests, including any protein exhibiting pesticidal or insect inhibitory activity if alignment of such protein with TIC4472, TIC4472PL, or TIC1425 results in amino acid sequence identity of any fraction percentage from about 93% to about 100% percent; or if alignment of such protein with TIC2613 or TIC2613PL results in amino acid sequence identity of any fraction percentage from about 73% to about 100% percent. The TIC4472, TIC4472PL, TIC1425, TIC2613, or TIC2613PL proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence describing a TIC4472, TIC4472PL, TIC1425, TIC2613, or TIC2613PL protein. A segment or fragment exhibiting insect inhibitory activity is also disclosed in this application if alignment of such segment or fragment, with the corresponding section of the TIC4472 protein set forth in SEQ ID NO:2, TIC4472PL protein set forth in SEQ ID NO:4, TIC1425 protein set forth in SEQ ID NO:6, results in amino acid sequence identity of any fraction percentage from about 93 to about 100 percent between the segment or fragment and the corresponding section of the TIC4472, TIC4472PL, or TIC1425 protein; or if alignment of such segment or fragment, with the corresponding section of the TIC2613 set forth in SEQ ID NO:8, or TIC2613PL protein set forth in SEQ ID NO:10, results in amino acid sequence identity of any fraction percentage from about 73 to about 100 percent between the segment or fragment and the corresponding section of the TIC2613 or TIC2613PL protein.

In still further specific embodiments, a fragment of a TIC4472, TIC4472PL, TIC1425, TIC2613, or TIC2613PL protein may be defined as exhibiting pesticidal activity possessed by the starting protein molecule from which it is derived. A fragment of a nucleic acid sequence encoding a TIC4472, TIC4472PL, TIC1425, TIC2613, or TIC2613PL protein may be defined as encoding a protein exhibiting the pesticidal activity possessed by the protein molecule encoded by the starting nucleic acid sequence from which it is derived. A fragment or variant described herein may further comprise a domain identified herein which is responsible for the pesticidal activity of a protein.

In specific embodiments, fragments of a TIC4472, TIC4472PL, TIC1425, TIC2613, or TIC2613PL protein are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, at least about 1000, at least about 1100, at least about 1150, or at least about 1175 contiguous amino acids, or longer, of a TIC4472, TIC4472PL, TIC1425, TIC2613, or TIC2613PL protein having pesticidal activity as disclosed herein. In certain embodiments, the invention provides fragments of any one of SEQ ID NOs: 2, 4, 6, 8, or 10, having the activity of the full length sequence. Methods for producing such fragments from a starting molecule are well known in the art.

Reference in this application to the terms "active" or "activity", "pesticidal activity" or "pesticidal" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC4472, TIC4472PL, TIC1425, TIC2613, or TIC2613PL protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry and Cyt proteins available in the art for use in controlling *Coleopteran, Hemipteran* and *Homopteran* species.

It is intended that reference to a pest, particularly a pest of a crop plant, means insect pests of crop plants, particularly those Lepidoptera insect pests that are controlled by the TIC4472, TIC4472PL, TIC1425, TIC2613, or TIC2613PL protein toxin class. However, reference to a pest can also include *Coleopteran, Hemipteran* and *Homopteran* insect pests of plants, as well as nematodes and fungi when toxic agents targeting these pests are co-localized or present together with the TIC4472, TIC4472PL, or TIC1425 protein or a protein that is 93 to about 100 percent identical to TIC4472, TIC4472PL, or TIC1425; or the TIC2613, or TIC2613PL protein or a protein that is 73 to about 100 percent identical to TIC2613, or TIC2613PL.

The TIC4472, TIC4472PL, TIC1425, TIC2613, or TIC2613PL proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera exempta*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leafminer (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in this application, an open reading frame (ORF) encoding TIC4747 (SEQ ID NO:1) was discovered in DNA obtained from *Bacillus thuringiensis* strain EG10742. The coding sequence was cloned and expressed in microbial host cells to produce recombinant proteins used in bioassays. An open reading frame (ORF) encoding TIC1425 (SEQ ID NO:5) was discovered in DNA obtained from *Bacillus thuringiensis* strain EG10731. An open reading frame (ORF) encoding TIC2613 (SEQ ID NO:7) was discovered in DNA obtained from *Bacillus thuringiensis* strain EG5408. Bioassay using microbial host cell-derived proteins of TIC4472 demonstrated activity against the Lepidopteran species Beet armyworm (*Spodoptera exigua*), Corn earworm (*Helicoverpa zea*), Cotton leaf worm (*Alabama argillacea*), European corn borer (*Ostrinia nubilalis*), Fall armyworm (*Spodoptera frugiperda*), Old World bollworm (*Helicoverpa armigera*), Oriental leaf worm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*). In addition, activity was also observed against Yellow fever mosquito (*Aedes aegypti*). Bioassay using microbial host cell-derived proteins of TIC1425 demonstrated activity against the Lepidopteran species Cotton leaf worm (*Alabama argillacea*), European corn borer (*Ostrinia nubilalis*), Fall armyworm (*Spodoptera frugiperda*), Sugarcane borer (*Diatraea saccharalis*), and Southwestern corn borer (*Diatraea grandiosella*. Bioassay using microbial host cell-derived proteins of TIC2613 demonstrated activity against the Lepidopteran species Corn earworm (*Helicoverpa zea*), Cotton leaf worm (*Alabama argillacea*), European corn borer (*Ostrinia nubilalis*), Fall armyworm (*Spodoptera frugiperda*), Soybean looper (*Chrysodeixis includens*), Southwestern corn borer (*Diatraea grandiosella*), and Tobacco budworm (*Heliothis virescens*).

For expression in plant cells, the TIC4472, TIC4472PL, TIC1425, TIC2613, or TIC2613PL proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC6757 or TIC6757PL toxin protein to the chloroplast, a sequence encoding a chloroplast transit peptide is placed 5' in operable linkage and in frame to a synthetic coding sequence encoding the TIC6757 or TIC6757PL toxin protein that has been designed for optimal expression in plant cells.

It is contemplated that additional toxin protein sequences related to TIC4472, TIC1425, or TIC2613 can be created by using the amino acid sequence of TIC4472, TIC1425, or TIC2613 to create novel proteins with novel properties. The TIC4472, TIC1425, or TIC2613 toxin proteins can be aligned to combine differences at the amino acid sequence level into novel amino acid sequence variants and making appropriate changes to the recombinant nucleic acid sequence encoding the variants.

This disclosure further contemplates that improved variants of the TIC4472 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence are altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC4472, TIC1425, or TIC2613 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC4472, TIC1425, or TIC2613 or derived protein variants, but should retain the insect inhibitory activity of at least TIC4472, TIC1425, or TIC2613. A fragment or variant described herein may further comprise a domain identified herein which is responsible for the pesticidal activity of a protein.

are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC4472, TIC4472PL, or TIC1425 if the protein is used in a query, e.g., in a Clustal W alignment, and the proteins of the present invention as set forth as SEQ ID NO:2, SEQ ID NO:4, or SEQ ID NO:6 are identified as hits in such alignment in which the query protein exhibits at least 93% to about 100% amino acid identity along the length of the query protein that is about 93%, 94%, 95%, 96%, 97%, 98%, 99%, 100%, or any fraction percentage in this range. It is also intended that a protein exhibiting insect inhibitory activity against a Lepidopteran insect species is related to TIC2613 or TIC2613PL if the protein is used in a query, e.g., in a Clustal W alignment, and the proteins of the present invention as set forth as SEQ ID NO:8, or SEQ ID NO:10 are identified as hits in such alignment in which the query protein exhibits at least 73% to about 100% amino acid identity along the length of the query protein that is about 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or any fraction percentage in this range Exemplary proteins TIC4472, TIC4472PL, TIC1425, TIC2613, and TIC2613PL were aligned with each other using a Clustal W algorithm. A pair-wise matrix of percent amino acid sequence identities for each of the full-length proteins was created, as reported in Table 1.

TABLE 1

Pair-wise matrix display of exemplary proteins TIC4472, TIC4472PL, TIC1425, TIC2613, and TIC2613PL.

| Toxin | TIC4472 (SEQ ID NO: 2) | TIC4472PL (SEQ ID NO: 4) | TIC1425 (SEQ ID NO: 6) | TIC2613 (SEQ ID NO: 8) | TIC2613PL (SEQ ID NO: 10) |
|---|---|---|---|---|---|
| TIC4472 (SEQ ID NO: 2) | — | 99.9 (1186) | 99.9 (1186) | 68.1 (808) | 68 (807) |
| TIC4472PL (SEQ ID NO: 4) | 99.8 (1186) | — | 99.7 (1185) | 67.9 (807) | 68.1 (809) |
| TIC1425 (SEQ ID NO: 6) | 99.9 (1186) | 99.8 (1185) | — | 68.2 (809) | 68.1 (808) |
| TIC2613 (SEQ ID NO: 8) | 68.6 (808) | 68.5 (807) | 68.7 (809) | — | 99.9 (1177) |
| TIC2613PL (SEQ ID NO: 10) | 68.4 (807) | 68.6 (809) | 68.5 (808) | 99.8 (1177) | — |

Table Description: Clustal W alignment between (X) and (Y) are reported in a pair-wise matrix. The percent amino acid identity between all pairs is calculated and is represented by the first number in each box. The second number (in parentheses) in each box represents the number of identical amino acids between the pair.

Proteins that resemble the TIC4472, TIC4472PL, TIC1425, TIC2613, and TIC2613PL proteins can be identified and compared to each other using various computer based algorithms known in the art (see Tables 1 and 2). Amino acid sequence identities reported in this application In addition to percent identity, TIC4472, TIC4472PL, TIC1425, TIC2613, and TIC2613PL and related proteins can also be related by primary structure (conserved amino acid motifs), by length (about 1187 amino acids), and by other characteristics. Characteristics of the TIC4472, TIC4472PL, TIC1425, TIC2613, and TIC2613PL protein toxins are reported in Table 2.

TABLE 2

Selected characteristics of the TIC4472, TIC4472PL, TIC1425, TIC2613, and TIC2613PL proteins.

| Protein | Molecular Weight (in Daltons) | Amino Acid Length | Isoelectric Point | Charge at PH 7.0 | No. of Strongly Basic (−) Amino Acids | No. of Strongly Acidic Amino Acids | No. of Hydrophobic Amino Acids | No. of Polar Amino Acids |
|---|---|---|---|---|---|---|---|---|
| TIC4472 | 134446.86 | 1187 | 4.7545 | −36 | 137 | 162 | 611 | 576 |
| TIC4472PL | 134517.94 | 1188 | 4.7545 | −36 | 137 | 162 | 612 | 576 |
| TIC1425 | 134460.88 | 1187 | 4.7545 | −36 | 137 | 162 | 611 | 576 |
| TIC2613 | 134636.07 | 1178 | 4.6653 | −42 | 132 | 162 | 588 | 590 |
| TIC2613PL | 134707.15 | 1179 | 4.6653 | −42 | 132 | 162 | 589 | 590 |

As described further in the Examples of this application, synthetic nucleic acid molecule sequences encoding a variant of TIC4472, TIC4472PL, and a variant of TIC2613, TIC2613PL, were designed for use in plants. An exemplary recombinant nucleic acid molecule sequence that was designed for use in plants encoding the TIC4472PL protein is presented as SEQ ID NO:3. An exemplary recombinant nucleic acid molecule sequence that was designed for use in plants encoding the TIC2613PL protein is presented as SEQ ID NO:9. The TIC4472PL and TIC2613PL proteins have an additional alanine amino acid immediately following the initiating methionine relative to the TIC4472 and TIC2613 proteins, respectively. The additional alanine residue inserted into the TIC4472 and TIC2613 amino acid sequences are believed to improve expression of the protein in planta. Likewise, synthetic nucleic acid molecule sequences encoding variants of TIC1425 and can designed for use in plants.

Leaf disc assay using $R_0$ cotton leaf tissue expressing TIC4472PL protein demonstrated high activity against Soybean looper (*Chrysodeixis includens*) and Tobacco budworm (*Heliothis virescens*) and low activity against Cotton bollworm (*Helicoverpa zea*) and Fall armyworm (*Spodoptera frugiperda*). Leaf disc assay using $R_0$ soybean leaf tissue expressing TIC4472PL protein demonstrated activity against Southern armyworm (*Spodoptera eridania*) and Soybean looper (*Chrysodeixis includens*).

Leaf samples from $R_0$ soybean plants expressing TIC4472PL and TIC2613PL proteins demonstrated activity against Southern armyworm (*Spodoptera eridania*) and Soybean looper (*Chrysodeixis includens*).

Expression cassettes and vectors containing a recombinant nucleic acid molecule sequence can be constructed and introduced into corn, soybean, cotton or other plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express TIC4472, TIC4472PL, TIC1425, TIC2613, and TIC2613PL proteins and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing. Similarly, a "recombinant protein molecule" is a protein molecule comprising a combination of amino acids that would not naturally occur together without human intervention. For example, a recombinant protein molecule may be a protein molecule that is comprised of at least two amino acid molecules heterologous with respect to each other, a protein molecule that comprises an amino acid sequence that deviates from amino acid sequences that exist in nature, or a protein molecule that is expressed in a host cell as a result of genetic transformation of the host cell or by gene editing of the host cell genome.

Recombinant nucleic acid molecule compositions that encode TIC4472, TIC4472PL, TIC1425, TIC2613, and TIC2613PL are contemplated. For example, TIC4472, TIC4472PL, TIC1425, TIC2613, and TIC2613PL proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC4472, TIC4472PL, TIC1425, TIC2613, or TIC2613PL protein encoding sequence for expression of the protein in plants or a Bt-functional promoter operably linked to a TIC4472, TIC4472PL, TIC1425, TIC2613, or TIC2613PL protein encoding sequence for expression of the protein in a Bt bacterium or other *Bacillus* species. Other elements can be operably linked to the TIC4472, TIC4472PL, TIC1425, TIC2613, or TIC2613PL protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:3, SEQ ID NO:1, SEQ ID NO:5, SEQ ID NO:7, and SEQ ID NO:9 that encodes the respective polypeptides or proteins having the amino acid sequence as set forth in SEQ ID NO:4, SEQ ID NO:2, SEQ ID NO:6, SEQ ID NO:8, and SEQ ID NO:10. A heterologous promoter can also be operably linked to synthetic DNA coding sequences encoding a plastid targeted TIC4472PL or TIC2613PL; or an untargeted TIC4472PL or TIC2613PL. The codons of a recombinant nucleic acid molecule encoding for proteins disclosed herein can be substituted by synonymous codons (known in the art as a silent substitution).

A recombinant DNA construct comprising TIC4472, TIC4472PL, TIC1425, TIC2613, or TIC2613PL protein encoding sequences can further comprise a region of DNA that encodes for one or more insect inhibitory agents which can be configured to concomitantly express or co-express with a DNA sequence encoding a TIC4472, TIC4472PL, TIC1425, TIC2613, or TIC2613PL protein, a protein different from a TIC4472, TIC4472PL, TIC1425, TIC2613, or TIC2613PL protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of TIC4472, TIC4472PL, TIC1425, TIC2613, or TIC2613PL are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC4472, TIC4472PL, TIC1425, TIC2613, or TIC2613PL protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC4472, TIC4472PL, TIC1425, TIC2613, or TIC2613PL protein encoding sequence in a host cell, or subsequent expression of the encoded polypeptide. An exogenous recombinant polynucleotide or recombinant DNA construct that comprises a TIC4472, TIC4472PL, TIC1425, TIC2613, or TIC2613PL protein encoding sequence and that is introduced into a host cell is referred in this application as a "transgene".

Transgenic bacteria, transgenic plant cells, transgenic plants, and transgenic plant parts that contain a recombinant polynucleotide that expresses any one or more of TIC4472 or a related family toxin protein encoding sequence are provided herein. The term "bacterial cell" or "bacterium" can include, but is not limited to, an *Agrobacterium*, a *Bacillus*, an *Escherichia*, a *Salmonella*, a *Pseudomonas*, a *Brevibacillus*, a *Klebsiella*, an *Erwinia*, or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory amounts of a TIC4472, TIC4472PL, TIC1425, TIC2613, or TIC2613PL protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC4472, TIC4472PL, TIC1425, TIC2613, or TIC2613PL protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC4472, TIC4472PL, TIC1425, TIC2613, or TIC2613PL protein.

Plants expressing the TIC4472, TIC4472PL, TIC1425, TIC2613, or TIC2613PL proteins can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

Reference in this application to an "isolated" DNA molecule or amino acid molecule, or an equivalent term or phrase, is intended to mean that the DNA molecule or amino acid molecule is one that is present alone or in combination with other compositions, but not within its natural environment. For example, a DNA molecule or amino acid molecule would be "isolated" within the scope of this disclosure so long as the element is not within the genome of the organism and at the location within the genome in which it is naturally found. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As further described in the Examples, TIC4472, TIC4472PL, TIC1425, TIC2613, or TIC2613PL protein-encoding sequences and sequences having a substantial percentage identity to TIC4472, TIC4472PL, TIC1425, TIC2613, or TIC2613PL can be identified using methods known to those of ordinary skill in the art such as polymerase chain reaction (PCR), thermal amplification and hybridization. For example, the proteins TIC4472, TIC4472PL, TIC1425, TIC2613, or TIC2613PL can be used to produce antibodies that bind specifically to related proteins, and can be used to screen for and to find other protein members that are closely related.

Furthermore, nucleotide sequences encoding the TIC4472, TIC4472PL, TIC1425, TIC2613, and TIC2613PL toxin proteins can be used as probes and primers for screening to identify other members of the class using thermalcycle or isothermal amplification and hybridization methods. For example, oligonucleotides derived from the sequence as set forth in SEQ ID NO:3 can be used to determine the presence or absence of a TIC4472PL transgene in a deoxyribonucleic acid sample derived from a commodity product. Oligonucleotides derived from the sequence as set forth in SEQ ID NO:7 can be used to determine the presence or absence of a TIC2613PL transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:3 or SEQ ID NO:9 can be used to detect a TIC4472PL or TIC2613PL transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NO:3 and SEQ ID NO:9. Such "mutagenesis" oligonucleotides are useful for identification of TIC4472PL and TIC2613PL amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as SEQ ID NO:3, SEQ ID NO:1, SEQ ID NO:5, SEQ ID NO:7, or SEQ ID NO:9 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise hybridization at a temperature of at least 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC4472, TIC4472PL, TIC1425, TIC2613, and TIC2613PL. This application contemplates the use of these and other identification methods known to those of ordinary skill in the art, to identify TIC4472, TIC1425, and TIC2613 protein-encoding sequences and sequences having a substantial percentage identity to TIC4472, TIC1425, and TIC2613 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC4472, TIC4472PL, TIC1425, TIC2613, or TIC2613PL, proteins to derive additional useful embodiments including assembly of segments of TIC4472, TIC4472PL, TIC1425, TIC2613, and TIC2613PL proteins with segments of diverse proteins different from TIC4472, TIC4472PL, TIC1425, TIC2613, and TIC2613PL and related proteins. The TIC4472, TIC4472PL, TIC1425, TIC2613, and TIC2613PL proteins may be subjected to alignment to each other and to other *Bacillus thuringiensis* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC4472, TIC4472PL, TIC1425, TIC2613, and TIC2613PL proteins are also disclosed in this application. Such methods can comprise growing a plant comprising an insect- or Lepidoptera-inhibitory amount of a TIC4472, TIC4472PL, TIC1425, TIC2613, and TIC2613PL toxin protein. In certain embodiments, such methods can further comprise any one or more of: (i) applying any composition comprising or encoding a TIC4472, TIC4472PL, TIC1425, TIC2613, and TIC2613PL toxin protein to a plant or a seed that gives rise to a plant; and (ii) transforming a plant or a plant cell that gives rise to a plant with a polynucleotide encoding a TIC4472, TIC4472PL, TIC1425, TIC2613, and TIC2613PL toxin protein. In general, it is contemplated that a TIC4472, TIC4472PL, TIC1425, TIC2613, and TIC2613PL toxin protein can be provided in a composition, provided in a microorganism, or provided in a transgenic plant to confer insect inhibitory activity against Lepidopteran insects.

In certain embodiments, a recombinant nucleic acid molecule of TIC4472, TIC4472PL, TIC1425, TIC2613, and TIC2613PL toxin proteins is the insecticidally active ingredient of an insect inhibitory composition prepared by culturing recombinant *Bacillus* or any other recombinant bacterial cell transformed to express a TIC4472, TIC4472PL, TIC1425, TIC2613, and TIC2613PL toxin protein under conditions suitable to express the TIC4472, TIC4472PL, TIC1425, TIC2613, and TIC2613PL toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC4472, TIC4472PL, TIC1425, TIC2613, and TIC2613PL can further comprise at least one additional polypeptide that exhibits insect inhibitory activity against the same Lepidopteran insect species, but which is different from the TIC4472, TIC4472PL, TIC1425, TIC2613, and TIC2613PL toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1l, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, axmi209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914). IP3 and variants thereof (U.S. Patent Publication 2012-0210462 A1), and ω-Hexatoxin-Hv1a (U.S. Patent Application Publication US2014-0366227 A1).

Additional polypeptides for the control of Coleopteran, Lepidopteran, and Hemipteran insect pests can be found on the Bacillus thuringiensis toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC4472, TIC4472PL, TIC1425, TIC2613, and TIC2613PL pesticidal proteins.

The aforementioned composition/formulation can further comprise an agriculturally-acceptable carrier, such as a bait, a powder, dust, pellet, granule, spray, emulsion, a colloidal suspension, an aqueous solution, a Bacillus spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC4472, TIC1425, and TIC2613

Sequences encoding three novel Bacillus thuringiensis pesticidal proteins were identified, cloned, sequence confirmed, and tested in insect bioassay. The pesticidal proteins, TIC4472, TIC1425 and TIC2613, isolated from the Bacillus thuringiensis strains EG10742, EG10731, and EG5408, respectively, represent novel Cry1Ca-like proteins.

Polymerase chain reaction (PCR) primers were designed to amplify a full length copy of the coding region for TIC4472, TIC1425 and TIC2613 from total genomic DNA isolated from the *Bacillus thuringiensis* strains EG10742, EG10731, and EG5408, respectively. The PCR amplicons also included the translational initiation and termination codons of each coding sequence.

Each of the amplicons were cloned using methods known in the art into Bt (*Bacillus thuringiensis*) expression vectors in operable linkage with a Bt expressible promoter.

Example 2

TIC4472, TIC1425, and TIC2613 Demonstrates Lepidopteran Activity in Insect Bioassay Bioactivity of the pesticidal proteins TIC4472, TIC1425 and TIC2613 was evaluated by producing the protein in a Bt expression host. A Bt strain expressing TIC4472, TIC1425 and TIC2613 was grown for twenty four (24) hours and then either a spore crystal preparation or solubilized protein preparation was added to insect diet. Mortality and stunting were evaluated by comparing the growth and development of insects on a diet with a culture from the Bt strain expressing TIC4472, TIC1425 and TIC2613 to insects on a diet with an untreated control culture.

Preparations of TIC4472 were assayed against the Lepidopteran species Corn earworm (two colonies (CEW and CEWUC), *Helicoverpa zea*, also herein referred to as Cotton bollworm and Soybean pod worm), Cotton leaf worm (CLW, *Alabama argillacea*), European corn borer (ECB, *Ostrinia nubilalis*), Fall armyworm (FAW, *Spodoptera frugiperda*), Soybean looper (SBL, *Chrysodeixis includens*), Southern armyworm (SAW, *Spodoptera eridania*), Southwestern corn borer (SWCB, *Diatraea grandiosella*), Sugarcane borer (SCB, *Diatraea saccharalis*), a Cry2Ab resistant colony of Sugarcane borer (SCB2R), Tobacco budworm (TBW, *Heliothis virescens*), and Velvet bean caterpillar (VBW, *Anticarsia gemmatalis*); the *Coleopteran* species Colorado potato beetle (CPB, *Leptinotarsa decemlineata*) and Western corn rootworm (WCB, *Diabrotica virgifera virgifera*); the *Hemipteran* species Tarnished plant bug (TPB, *Lygus lineolaris*), Western tarnished plant bug (WTP, *Lygus hesperus*); and the *Dipteran* species Yellow fever mosquito (*Aedes aegypti*). Preparations of TIC1425 were assayed against the Lepidopteran species Black cutworm (BCW, *Agrotis ipsilon*), Cotton leaf worm (CLW, *Alabama argillacea*), European corn borer (ECB, *Ostrinia nubilalis*), Fall armyworm (FAW, *Spodoptera frugiperda*), Black cutworm (BCW, *Agrotis ipsilon*), Southwestern corn borer (SWCB, *Diatraea grandiosella*), and Sugarcane borer (SCB, *Diatraea saccharalis*); and the *Coleopteran* species Western corn rootworm (WCB, *Diabrotica virgifera virgifera*) and Southern corn rootworm (*Diabrotica undecimpunctata howardi*). Preparations of TIC2613 were assayed against the Lepidopteran species Corn earworm (two colonies (CEW and CEWUC), *Helicoverpa zea*, also herein referred to as Cotton bollworm and Soybean pod worm), Cotton leaf worm (CLW, *Alabama argillacea*), European corn borer (ECB, *Ostrinia nubilalis*), Fall armyworm (FAW, *Spodoptera frugiperda*), Soybean looper (SBL, *Chrysodeixis includens*), Southern armyworm (SAW, *Spodoptera eridania*), Black cutworm (BCW, *Agrotis ipsilon*), Southwestern corn borer (SWCB, *Diatraea grandiosella*), Tobacco budworm (TBW, *Heliothis virescens*), and Velvet bean caterpillar (VBW, *Anticarsia gemmatalis*); the *Coleopteran* species Colorado potato beetle (CPB, *Leptinotarsa decemlineata*); Western corn rootworm (WCB, *Diabrotica virgifera virgifera*) and Southern corn rootworm (*Diabrotica undecimpunctata howardi*); and the *Hemipteran* species Tarnished plant bug (TPB, *Lygus lineolaris*), Western tarnished plant bug (WTP, *Lygus hesperus*).

The bioassay activity observed for each protein grown in the Bt host is presented in Tables 3 and 4 below, wherein "+" indicates activity, "NT" indicates the toxin was not assayed against that specific insect pest, "S" indicates stunting, and "M" indicates mortality. Preparations of TIC4472, TIC1425, and TIC2613 did not demonstrate activity against the *Coleopteran* or the *Hemipteran* insect pests assayed for each protein. TIC4472 also demonstrated activity against Yellow fever mosquito (*Aedes aegypti*). All three toxins demonstrated resistance to multiple Lepidopteran insect pests as shown in Tables 3 and 4.

TABLE 3

Bioassay activity of TIC4472, TIC1425, and TIC2613 against insect pests.

| Toxin | CEW | | CEWUC | | CLW | | ECB | | FAW | | SBL | | SAW | |
|---|---|---|---|---|---|---|---|---|---|---|---|---|---|---|
| | S | M | S | M | S | M | S | M | S | M | S | M | S | M |
| TIC4472 | + | + | + | + | + | + | + | + | + | | + | + | + | + |
| TIC1425 | NT | NT | | | | | + | + | + | + | NT | NT | | |
| TIC2613 | + | | | | + | + | + | + | + | + | + | + | + | |

TABLE 4

Bioassay activity of TIC4472, TIC1425, and TIC2613 against insect pests.

| Toxin | BCW | | SCB | | SCB2R | | SWCB | | TBW | | VBC | | YFM | |
|---|---|---|---|---|---|---|---|---|---|---|---|---|---|---|
| | S | M | S | M | S | M | S | M | S | M | S | M | S | M |
| TIC4472 | NT | NT | + | + | + | + | + | + | + | + | + | + | | + |
| TIC1425 | | | | + | NT | NT | | + | NT | NT | NT | NT | NT | NT |
| TIC2613 | | | | + | NT | NT | + | + | + | | | + | NT | NT |

As can be seen in Tables 3 and 4 above, the insect toxin TIC4472 demonstrated activity against all Lepidopteran insect pests assayed (CEW, CEWUC, CLW, ECB, FAW, SBL, SAW, SCB, SCB2R, SWCB, TBW, and VBC); as well as YFM. The insect toxin TIC1425 demonstrated activity against CLW, ECB, FAW, SCB, and SWCB. The insect toxin TIC2613 demonstrated activity against CEW, CLW, ECB, FAW, SBL, SAW, SCB, SWCB, TBW, and VBC. Activity was not observed for TIC1425 and TIC2613 when assayed against BCW.

In a separate series of experiments, protein preparations of TIC4472 were assayed using a diet overlay assay against the Lepidopteran insect pests Beet armyworm (BAW, *Spodoptera exigua*), Pink bollworm (PBW, *Pectinophora gossypiella*), Cry1Ac resistant Pink bollworm (PBW_Cry1Ac$^r$, *Pectinophora gossypiella*), Old world bollworm (OWB, *Helicoverpa armigera*), Oriental leaf worm (OLW, *Spodoptera litura*), and Spotted bollworm (SBW, *Earias vittella*). Table 5 shows the activity observed against each of these Lepidopteran insect pests assayed in the diet overlay bioassay, wherein "+" indicates activity.

TABLE 5

Bioassay activity of TIC4472 against Lepidopteran insect pests.

| BAW | PBW | PBW_Cry1Ac$^r$ | OWB | OLW | SBW |
|---|---|---|---|---|---|
| + | + | + | + | + | + |

Lepidopteran Insect Pest

As can be seen in Table 5 above, TIC4472 demonstrated activity against all of the Lepidopteran insect pests assayed in the diet overlay bioassay, including the Cry1Ac resistant colony of Pink bollworm.

As demonstrated in Tables 3-5, TIC4472, TIC1425, and TIC2613 demonstrate activity across a wide range of Lepidopteran insect pest species.

Example 3

Design of Synthetic Coding Sequences Encoding TIC4472PL and TIC2613PL for Expression in Plant Cells Synthetic coding sequences were constructed for use in expression of the encoded protein in plants, cloned into a binary plant transformation vectors, and used to transform plant cells. The synthetic sequences were synthesized according to methods generally described in U.S. Pat. No. 5,500,365, avoiding certain inimical problem sequences such as ATTTA and A/T rich plant polyadenylation sequences. The synthetic coding sequences encode TIC4472PL and TIC2613PL proteins which comprise an additional alanine residue immediately following the initiating methionine relative to the TIC4472 and TIC2613 proteins, respectively. The additional alanine residue is incorporated into the synthetic coding sequence to improve expression of the insect toxin protein.

The synthetic coding sequence encoding TIC4472PL (SEQ ID NO:4) is presented herein as SEQ ID NO:3. The synthetic coding sequence encoding TIC2613PL (SEQ ID NO:10) is presented as SEQ ID NO:9. The synthetic coding sequences were used in binary plant transformation vectors to generate transgenic plants expressing the TIC4472PL and TIC2613PL proteins and assayed for activity against Lepidopteran insect pests.

Example 4

Assay of TIC4472PL Activity Against Lepidopteran Pests in Stably Transformed Cotton Plants Binary plant transformation vectors comprising transgene cassettes designed to express untargeted TIC4472PL pesticidal protein were cloned using methods known in the art. The resulting vectors were used to stably transform cotton plants. Tissues were harvested from the transformants and used in insect bioassay against various Lepidopteran insect pests.

Synthetic coding sequences were constructed for use in expression of the encoded protein in plants, cloned into a binary plant transformation vector, and used to transform cotton plant cells. The resulting plant transformation vectors comprised a first transgene cassette for expression of the TIC4472PL pesticidal protein which comprised a constitutive promoter, operably linked 5' to a leader, operably linked 5' to a synthetic coding sequence encoding an untargeted TIC4472PL protein, which was in turn operably linked 5' to a 3' UTR; and a second transgene cassette for the selection of transformed plant cells using spectinomycin selection.

Three binary plant transformation vector constructs were constructed as described above and comprised different constitutive promoters. Two constructs, Construct 1 and Construct 3 also comprised an intron sequence that was operably linked 3' to the leader and 5' to the synthetic coding sequence encoding an untargeted TIC4472PL protein. Construct 2 was intronless. Cotton plants were transformed with the three different binary transformation vectors using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed cotton plant was used to obtain tissue to be used as a negative control. Multiple transformation $R_0$ single-copy insertion events from each binary vector were assessed against Cotton bollworm (CBW, *Helicoverpa zea*), Fall armyworm (FAW, *Spodoptera frugiperda*), Soybean looper (SBL, *Chrysodeixis includens*), and Tobacco budworm (TBW, *Heliothis virescens*). Leaf Damage Rating (LDR) scores ranging from one (1) to four (4) were applied to event. The LDR scores are based upon the percentage of damage observed for each leaf disc. Table 6 below shows the LDR scores and corresponding range of percent damage associated with each score. For LDR scores of one (1), the penetrance of the trait is also assessed. High penetrance (as indicated by "(H)") is defined as greater than fifty (50) percent of the assayed events for each construct having less than or equal to ten (10) percent leaf damage. Low penetrance (as indicated by "(L)") is defined as less than or equal to fifty (50) percent of the assayed events for each construct having less than or equal to ten (10) percent leaf damage. Penetrance is not applied to LDR scores greater than one (1).

TABLE 6

Cotton Leaf Damage Rating (LDR) scores and corresponding percentage damage and Penetrance.

| LDR Score | Leaf Damage Rating (LDR) range | Penetrance |
|---|---|---|
| 1 | LDR ≤ 10% | High = >50% of events |
| 1 | | Low = <50% of events |
| 2 | 10% < LDR ≤ 17.5% | n/a |
| 3 | 17.5% < LDR ≤ 35% | n/a |
| 4 | LDR > 35% | n/a |

The leaf damage rating scores for transformed $R_0$ cotton plants expressing TIC4472PL are presented in Table 7 below. The number of events demonstrating the LDR score out of the total number events assayed is shown in parenthesis, followed by the penetrance for those LDR scores of one (1).

TABLE 7

Leaf Damage Rating (LDR) scores, number of events demonstrating the LDR, and penetrance for transformed $R_0$ cotton plants expressing TIC4472PL.

| Construct | CBW | FAW | SBL | TBW |
|---|---|---|---|---|
| Construct 1 | 3 (1/25) | 2 (2/25) | 1 (25/25) H | 1 (24/25) H |
| Construct 2 | 3 (3/25) | 2 (1/25) | 1 (24/25) H | 1 (16/25) H |
| Construct 3 | 4 (23/23) | 1 (1/23) L | 1 (21/23) H | 1 (6/23) L |

Transformed $R_0$ cotton plants expressing TIC4472PL were highly efficacious (defined as having less than or equal to ten percent leaf damage) against SBL and TBW as shown in Table 7. Activity against CBW and FAW was also observed in several events.

$R_1$ cotton events were selected from the transformed $R_0$ cotton plants assayed above and were used in a leaf disc assay against FAW, SBL, and TBW. Table 8 shows the leaf damage rating scores for transformed $R_1$ cotton plants expressing TIC4472PL.

TABLE 8

Leaf Damage Rating (LDR) scores, number of events demonstrating the LDR, and penetrance for transformed $R_1$ cotton plants expressing TIC4472PL.

| Construct | FAW | SBL | TBW |
|---|---|---|---|
| Construct 1 | 1 (3/4) H | 1 (4/4) H | 1 (4/4) H |
| Construct 2 | 1 (1/4) L | 1 (4/4) H | 1 (1/4) L |

As can be seen in Table 8 above, the selected events showed high efficacy against FAW, SBL, and TBW. Penetrance was high for Construct 1 transformed events for all three insect pest species. With respect to Construct 2 transformed events, penetrance was high for SBL.

The forgoing demonstrates that transformed cotton plants expressing TIC4472PL protein provide resistance to Fall armyworm (FAW, *Spodoptera frugiperda*), Soybean looper (SBL, *Chrysodeixis includens*) and Tobacco budworm (TBW, *Heliothis virescens*).

Example 5

Assay of TIC4472PL and TIC2613PL Activity Against Lepidopteran Pests in Stably Transformed Soybean Plants A binary plant transformation vector comprising a transgene cassette designed to express a plastid targeted TIC4472PL or TIC2613PL untargeted pesticidal protein was cloned using methods known in the art. The resulting vector was used to stably transform soybean plants. Tissues were harvested from the transformants and used in insect bioassay against various Lepidopteran insect pests.

The synthetic coding sequences designed for plant expression described in Example 3 were cloned into binary plant transformation vector constructs, and used to transform soybean plant cells. Three binary vector constructs were constructed using methods known in the art to express plastid targeted and untargeted TIC4472PL. Construct 4 comprised a first transgene cassette for expression of the untargeted TIC4472PL which comprised a constitutive promoter, operably linked 5' to a leader, operably linked 5' to a synthetic coding sequence encoding an untargeted TIC4472PL protein, which was in turn operably linked 5' to a 3' UTR and; a second transgene cassette for the selection of transformed plant cells using spectinomycin selection. Construct 5 comprised a first transgene cassette for expression of the targeted TIC4472PL which comprised a constitutive promoter, operably linked 5' to a leader, operably linked 5' to an intron, operably linked 5' to a synthetic coding sequence encoding a plastid targeted TIC4472PL protein, which was in turn operably linked 5' to a 3' UTR and; a second transgene cassette for the selection of transformed plant cells using spectinomycin selection. Construct 6 comprised a first transgene cassette for expression of the untargeted TIC4472PL which comprised a constitutive promoter, operably linked 5' to a leader, operably linked 5' to an intron, operably linked 5' to a synthetic coding sequence encoding an untargeted TIC4472PL protein, which was in turn operably linked 5' to a 3' UTR and; a second transgene cassette for the selection of transformed plant cells using spectinomycin selection.

Two binary vector constructs were constructed using methods known in the art to express untargeted TIC2613PL. Construct 7 comprised a first transgene cassette for expression of the untargeted TIC2613PL which comprised a constitutive promoter, operably linked 5' to a leader, operably linked 5' to a synthetic coding sequence encoding an untargeted TIC2613PL protein, which was in turn operably linked 5' to a 3' UTR and; a second transgene cassette for the selection of transformed plant cells using spectinomycin selection. Construct 8 comprised a first transgene cassette for expression of the untargeted TIC2613PL which comprised a constitutive promoter, operably linked 5' to a leader, operably linked 5' to an intron, operably linked 5' to a synthetic coding sequence encoding an untargeted TIC2613PL protein, which was in turn operably linked 5' to a 3' UTR and; a second transgene cassette for the selection of transformed plant cells using spectinomycin selection.

The resulting binary transformation vector constructs were used to transform soybean cells using an *Agrobacterium*-mediated transformation method. The transformed soybean cells were induced to form plants by methods known in the art. Bioassays using plant leaf disks were performed analogous to those described in U.S. Pat. No. 8,344,207. A non-transformed soybean plant was used to obtain tissue to be used as a negative control. Multiple $R_0$ soybean transformation events derived from the binary vectors were assessed against Southern armyworm (SAW, *Spodoptera eridania*), Soybean looper (SBL, *Chrysodeixis includens*), and Soybean podworm (SPW, *Helicoverpa zea*). The Leaf Damage Rating (LDR) scores were similar to those as for cotton but differed in the range of percentage damage used to determine the score. The Leaf Damage Rating scores and their corresponding percent leaf damage rating range are presented in Table 9 below.

TABLE 9

Soybean Leaf Damage Rating (LDR) scores and corresponding percentage damage range.

| LDR Score | Leaf Damage Rating (LDR) range |
|---|---|
| 1 | LDR ≤ 20% |
| 2 | 20% < LDR ≤ 35% |
| 3 | 35% < LDR ≤ 70% |
| 4 | LDR > 70% |

The leaf damage rating scores for transformed $R_0$ cotton plants expressing TIC4472PL and TIC2613PL are presented in Table 10 below. The number of events demonstrating the LDR score out of the total number events assayed is shown in parenthesis.

TABLE 10

Leaf Damage Rating (LDR) scores and number of events demonstrating the LDR for transformed $R_0$ soybean plants expressing TIC4472PL and TIC2613PL.

| Toxin | Construct | SAW | SBL | SPW |
|---|---|---|---|---|
| TIC4472PL | Construct 4 | 1 (23/29) | 1 (29/29) | 3 (8/29) |
| TIC4472PL | Construct 5 | 1 (20/29) | 1 (28/29) | 1 (1/29) |
| TIC4472PL | Construct 6 | 1 (10/29) | 1 (15/15) | 3 (3/15) |
| TIC2613PL | Construct 7 | 1 (22/30) | 1 (24/30) | 3 (1/30) |
| TIC2613PL | Construct 8 | 1 (14/25) | 1 (22/25) | 2 (2/25) |

As can be seen in Table 10 above, both expression of both TIC4472PL and TIC2613PL demonstrated high efficacy against SAW and SBL. Activity was lower for both proteins against SPW.

$R_1$ soybean events were selected from the transformed $R_0$ soybean plants expressing TIC4472PL and TIC2613PL assayed above and were used in a leaf disc assay against SAW, SBL, and SPW. A $R_1$ soybean event expressing TIC4472PL was also assessed against Velvet bean caterpillar (VBW, *Anticarsia gemmatalis*). Table 11 shows the leaf damage rating scores for transformed $R_1$ soybean plants expressing TIC4472PL and TIC2613PL.

TABLE 11

Leaf Damage Rating (LDR) scores and number of events demonstrating the LDR for transformed $R_1$ soybean plants expressing TIC4472PL and TIC2613PL.

| Toxin | Construct | SAW | SBL | SPW | VBC |
|---|---|---|---|---|---|
| TIC4472PL | Construct 5 | 1 (3/8) | 1 (5/8) | 3 (2/8) | |
| TIC4472PL | Construct 6 | 1 (1/9) | 1 (6/9) | 3 (1/9) | 1 (3/9) |
| TIC2613PL | Construct 8 | 2 (2/10) | 1 (9/10) | 4 (4/10) | |

As can be seen in Table 11, a number of $R_1$ soybean events transformed with TIC4472PL demonstrated high efficacy against SAW and SBL. In addition, several $R_1$ soybean events transformed using Construct 6 demonstrated high efficacy against VBC. $R_1$ soybean events transformed with TIC2613PL demonstrated high efficacy against SBL.

The forgoing demonstrates that transformed soybean plants expressing TIC4472PL or TIC2613PL provide resistance to Lepidopteran insects, in particular Southern armyworm (*Spodoptera eridania*) and Soybean looper (*Chrysodeixis includens*) and Velvet bean caterpillar (*Anticarsia gemmatalis*).

Example 6

Assay of TIC4472PL and TIC2613PL Activity Against Lepidopteran Pests in Stably Transformed Corn Plants Binary plant transformation vectors comprising transgene cassettes designed to express both plastid targeted and untargeted TIC4472PL or TIC2613PL pesticidal protein are cloned using methods known in the art. The resulting vectors are used to stably transform corn plants. Tissues are harvested from the transformants and used in insect bioassay against various Lepidopteran insect pests.

The synthetic coding sequence encoding TIC4472PL (SEQ ID NO:3) or TIC2613 (SEQ ID NO:9) protein are cloned into binary transformation vectors. For plastid targeted protein, the synthetic TIC4472PL or TIC2613PL pesticidal protein coding sequence is operably linked in frame with a chloroplast targeting signal peptide encoding sequence. The resulting plant transformation vectors comprise a first transgene cassette for expression of the TIC4472PL or TIC2613PL pesticidal protein which comprise a constitutive promoter, operably linked 5' to a leader, operably linked 5' to an intron, operably linked 5' to a synthetic coding sequence encoding a plastid targeted or untargeted TIC4472PL or TIC2613PL protein, which is in turn operably linked 5' to a 3' UTR; and a second transgene cassette for the selection of transformed plant cells using glyphosate selection.

Corn plants are transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn plant is used to obtain tissue to be used as a negative control. Multiple transformation events from each binary vector are assessed against Beet armyworm (BAW, *Spodoptera exigua*), Black cutworm (BCW, *Agrotis ipsilon*), Corn earworm (CEW, *Helicoverpa zea*), Cotton leaf worm (CLW, *Alabama argillacea*), European corn borer (ECB, *Ostrinia nubilalis*), Fall armyworm (FAW, *Spodoptera frugiperda*), Old world bollworm (OWB, *Helicoverpa armigera*), Oriental leaf worm (OLW, *Spodoptera litura*), Pink bollworm (PBW, *Pectinophora gossypiella*), Soybean looper (SBL, *Chrysodeixis includens*), Spotted bollworm (SBW, *Earias vittella*), Southwestern corn borer (SWCB, *Diatraea grandiosella*), Sugarcane borer (SCB, *Diatraea saccharalis*), Tobacco budworm (TBW, *Heliothis virescens*), and Velvet bean caterpillar (VBW, *Anticarsia gemmatalis*), as well as other Lepidopteran insect pests.

The insect pests are observed for mortality and stunting caused by ingestion of the presented leaf discs expressing TIC4472PL or TIC2613PL and compared to leaf discs derived from non-transformed corn plants.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein or pesticidal fragment thereof, wherein:
   a. said pesticidal protein comprises the amino acid sequence of SEQ ID NO: 10; or said pesticidal protein comprises an amino add sequence having at least 90%, or 95%, or about 100% amino add sequence identity to SEQ ID NO:10; or
   b. said polynucleotide segment hybridizes under stringent hybridization conditions to a polynucleotide having the nucleotide sequence of SEQ ID NO:9.

2. The recombinant nucleic acid molecule of claim 1, wherein:
   a. the recombinant nucleic acid molecule comprises a sequence that functions to express the pesticidal protein in a plant; or
   b. the recombinant nucleic acid molecule is expressed in a plant cell to produce a pesticidally effective amount of the pesticidal protein; or
   c. the recombinant nucleic acid molecule is in operable linkage with a vector, and said vector is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial and a plant cell.

4. The host cell of claim 3, wherein the bacterial host cell is from a genus of bacteria selected from the group consisting of: *Agrobacterium, Rhizobium, Bacillus, Brevibacillus, Escherichia, Pseudomonas, Klebsiella, Pantoea,* and *Erwinia.*

5. The host cell of claim 4, wherein the *Bacillus* species is *Bacillus cereus* or *Bacillus thuringiensis*, said *Brevibacillus* is *Brevibacillus laterosperous*, and said *Escherichia* is *Escherichia coli.*

6. The host cell of claim 3, wherein said plant cell is a dicotyledonous or a monocotyledonous plant cell.

7. The host cell of claim 6, wherein said plant host cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said protein exhibits activity against a Lepidopteran insect.

9. The recombinant nucleic acid molecule of claim 8, wherein said insect is selected from the group consisting of: Beet armyworm (*Spodoptera exigua*), Corn earworm (*Helicoverpa zea*), Cotton leaf worm (*Alabama argillacea*), European corn borer (*Ostrinia nubilalis*), Fall armyworm (*Spodoptera frugiperda*), Old World bollworm (*Helicoverpa armigera*), Oriental leaf worm (*Spodoptera litura*), Pink bollworm (*Pectinophora gossypiella*), Cry1Ac resistant Pink bollworm (*Pectinophora gossypiella*), Soybean looper (*Chrysodeixis includens*), Southern armyworm (*Spodoptera eridania*), Southwestern corn borer (*Diatraea grandiosella*), Spotted bollworm (*Earias vittella*), Sugarcane borer (*Diatraea saccharalis*), Tobacco budworm (*Heliothis virescens*), and Velvet bean caterpillar (*Anticarsia gemmatalis*).

10. A plant or part thereof comprising the recombinant nucleic acid molecule of claim 1.

11. The plant or part thereof of claim 10, wherein said plant is a monocot plant or a dicot plant.

12. The plant of claim 10, wherein the plant is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

13. A seed of the plant of claim 10, wherein said seed comprises said recombinant nucleic acid molecule.

14. An insect inhibitory composition comprising the recombinant nucleic acid molecule of claim 1.

15. The insect inhibitory composition of claim 14, further comprising a nucleotide sequence encoding at least one other pesticidal agent that is different from said pesticidal protein.

16. The insect inhibitory composition of claim 15, wherein said at least one other pesticidal agent is selected from the group consisting of an insect inhibitory protein, an insect inhibitory dsRNA molecule, and an ancillary protein.

17. The insect inhibitory composition of claim 16, wherein said at least one other pesticidal agent exhibits activity against one or more pest species of the orders Lepidoptera, Coleoptera, or Hemiptera.

18. The insect inhibitory composition of claim 17, wherein said at least one other pesticidal protein is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 and a DIG-11 protein.

19. The insect inhibitory composition of claim 14, defined as comprising a plant cell that expresses said recombinant nucleic acid molecule.

20. A commodity product produced from the plant or part thereof of claim 10, wherein the commodity product comprises a detectable amount of said recombinant nucleic acid molecule or a pesticidal protein.

21. The commodity product of claim 20, selected from the group consisting of commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

22. A method of producing seed comprising:
    a. planting a first seed according to claim 13;
    b. growing a plant from the seed; and
    c. harvesting seed from the plants, wherein said harvested seed comprises said recombinant nucleic acid molecule.

23. A plant resistant to insect infestation, wherein the cells of said plant comprise the recombinant nucleic acid molecule of claim 1.

24. A method for controlling a Lepidopteran species pest or pest infestation, said method comprising:
    a. contacting the pest with an insecticidally effective amount of a pesticidal protein as set forth in SEQ ID NO: 10; or contacting the pest with an insecticidally effective amount of one or more pesticidal proteins comprising an amino acid sequence having at least 90%, or 95%, or about 100% amino acid sequence identity to SEQ ID NO:10.

25. A method of detecting the presence of the recombinant nucleic acid molecule of claim 1 in a sample comprising plant genomic DNA, comprising:
    a. contacting the sample with a nucleic acid probe that hybridizes under stringent hybridization conditions with genomic DNA from a plant comprising the DNA molecule of claim 1, and does not hybridize under such hybridization conditions with genomic DNA from an otherwise isogenic plant that does not comprise the recombinant nucleic acid molecule of claim 1, wherein the probe is homologous or complementary to SEQ ID NO:9, or a sequence that encodes a pesticidal protein comprising an amino acid sequence having at least 90%, or 95%, or about 100% amino acid sequence identity to SEQ ID NO:10;
    b. subjecting the sample and probe to stringent hybridization conditions; and
    c. detecting hybridization of the probe with DNA of the sample.

26. A method of detecting the presence of a pesticidal protein or fragment thereof in a sample comprising protein, wherein said pesticidal protein comprises the amino acid sequence of SEQ ID NO: 10; or said pesticidal protein comprises an amino acid sequence having at least 90%, or 95%, or about 100% amino acid sequence identity to SEQ ID NO: 10; comprising:

a. contacting the sample with an immunoreactive antibody; and b. detecting the presence of the protein.

27. The method of claim 26, wherein the step of detecting comprises an ELISA, or a Western blot.

28. The recombinant nucleic acid molecule of claim 1, wherein said pesticidal protein comprises the amino acid sequence of SEQ ID NO:10.

29. The recombinant nucleic acid molecule of claim 1, wherein said pesticidal protein comprises an amino acid sequence having at least 90% amino acid sequence identity to SEQ ID NO:10.

30. The recombinant nucleic acid molecule of claim 1, wherein said pesticidal protein comprises an amino acid sequence having at least 95% amino acid sequence identity to SEQ ID NO:10.

31. The recombinant nucleic acid molecule of claim 1, wherein said pesticidal protein comprises an amino acid sequence having about 100% amino acid sequence identity to SEQ ID NO:10.

32. The recombinant nucleic acid molecule of claim 1, wherein said polynucleotide segment hybridizes under stringent hybridization conditions to a polynucleotide having the nucleotide sequence of SEQ ID NO:9.

\* \* \* \* \*

SEQUENCE LISTING

<160> NUMBER OF SEQ ID NOS: 10

<210> SEQ ID NO 1
<211> LENGTH: 3564
<212> TYPE: DNA
<213> ORGANISM: Bacillus thuringienses
<220> FEATURE:
<221> NAME/KEY: misc_feature
<222> LOCATION: (1)..(3564)
<223> OTHER INFORMATION: Nucleic acid sequence encoding a TIC4472
    pesticidal protein obtained from Bacillus thuringiensis species
    EG10742.

<400> SEQUENCE: 1

| | | | | | |
|---|---|---|---|---|---|
| atgaataata | atattgaaaa | ccaatgcgta | ccttacaatt | gtttaagtaa | tcctgaagaa | 60 |
| gtaattttgg | atggagaacg | gatatcaact | ggtaattcat | caattgatat | ttctctgtca | 120 |
| cttgttcaac | ttctggtatc | taactttgta | ccaggcggag | gattttagt | agggttaata | 180 |
| gattttgtat | ggggaatagt | aggcccttct | ccatgggatg | catttctagt | gcaaattgaa | 240 |
| caattaattc | agcaaagaat | agaagcatat | gctagggctg | cagcaatttc | taatttagaa | 300 |
| ggaataggaa | acaatttcaa | tatatatgtg | aagcatttc | aagaatggga | agaagatcct | 360 |
| aataatccag | caaccaggaa | tagagtagtt | gatcgctttc | gtatacttga | tgggctactt | 420 |
| gaaagggaca | ttccttcgtt | tcgaatttct | ggatttgaag | tccccctttt | atccgtttat | 480 |
| gctcaagcgg | ccaatctgca | tctagctata | ttaagagatt | ctgtaatttt | tggagaaaga | 540 |
| tggggattga | caacaacaaa | tgtcaatgaa | actataata | gacaaatcag | gcatattgat | 600 |
| gaatatgctg | atcactgtgc | aaatacgtat | aatcggggat | taaataattt | accgaaatct | 660 |
| acgtatcaag | attggataac | atataatcga | ttacggagag | aattaacatt | gactgtatta | 720 |
| gatatcgctg | ctttctttcc | aaactatgac | aataggcggt | atccaattca | gccagttggt | 780 |
| caactaacaa | gggaagttta | tacggaccca | ttaattactt | ttaatcccca | gttacagtct | 840 |
| gtagctcaat | tacctacttt | taacgttatg | gaaagcaacg | caattagaaa | tcctcatttg | 900 |
| tttgatatat | tgaataatct | tacaatttt | acggattggt | ttagtgttgg | acgcaacttt | 960 |
| tattggggag | acatcgagt | aacttctaac | tatataggag | gaggcaacat | aacatctcct | 1020 |
| atatatggaa | gagaggcgaa | ccaggagcct | ccaagatctt | ttacttttaa | tggacctgtt | 1080 |
| tttaggactt | tatcaaatcc | tactttacga | ttattacagc | aaccttggcc | agcaccacca | 1140 |
| tttaatttac | gtggtgttga | aggagtagaa | ttttctacac | ctacaaatag | ctttacgtat | 1200 |
| cgaggaagag | gtacagttga | ttctttaacc | gaattaccgc | ctgaggataa | tagtgtgcta | 1260 |
| cctcgcgagg | gatatagtca | tcgtttatgt | catgcaactt | tgttcaaag | atctggaaca | 1320 |
| ccatttttaa | caacgggtgt | agtattttct | tggacgcatc | gcagtgcaac | tcttacaaat | 1380 |
| acaattgatc | cagacaaaat | tactcagata | cctttagtga | aaggatttag | agtttggagt | 1440 |
| ggcgcctctg | tcgttacagg | accaggtttt | acaggagggg | atatccttcg | aagaactaac | 1500 |
| tttggggatt | ttgtatctat | gcaagttaat | attaattcac | caataacaca | aagataccgt | 1560 |
| ttaagatttc | gttatgcttc | cagtagagat | gcacgactta | cagtagcgac | aggagcagca | 1620 |
| aacacaggag | ttggagggca | aattagtgtg | gacatggctc | ttcagaaaac | tatgaaatt | 1680 |
| ggagagagct | aacatctag | aacatttaga | tataccgatt | ttagtaatcc | ttttcatttt | 1740 |
| agagctaatc | cagatataat | tcgtataaat | gaacaaccac | tattcggtgc | aggctctatt | 1800 |
| agtagtggtg | aactttatat | agataaaatt | gaaattattc | tagcagatgc | aacatttgaa | 1860 |
| gcagaatatg | atttggaaag | agcacagaag | gcggtgaatg | cgctgtttac | ttctacaaac | 1920 |

-continued

```
caaagaggat taaaaacaga tgtgacggat tatcatattg atcaagtatc caatttagtt    1980
gagtgtttat cggatgaatt ttgtctggat gaaaaacgag aattgtccga gaaagtcaaa    2040
catgcgaagc gactcagtga tgagcgaaat ttactccagg atcgaaattt cacatccatt    2100
aatgggcaac tagaccgtgg ctggagagga agtacggata ttaccatcca aggaggagat    2160
gacgtattca agagaatta cgtcacacta ctgggtacct ttgatgagtg ctatccaacg     2220
tatttatatc aaaaaataga tgagtcgaaa ttaaaagcct atacccgcta tgaattaaga    2280
gggtatatcg aggatagtca agacttagaa atctatttaa ttcgctacaa tgcaaaacac    2340
gaaacagtaa atgtgccagg tacaggttcc ttatggccgc tttcagtcga agtccaatc    2400
ggaaagtgtg agaaccgaa tcgatgcaca ccacaccttg aatggaatcc taatctagat    2460
tgttcctgca gagacgggaa acatgtgca catcattctc atcatttctc cttggacatt    2520
gatgttggat gtacagactt aaatgaagat ctaggtgtat gggtgatatt caagattaag    2580
acgcaagatg gtcatgcaag actaggaaat ctagagtttc tcgaagagaa accattagta    2640
ggagaagcgt tagctcgtgt gaaaagagcg gagaaaaaat ggagagacaa acgcgaaaaa    2700
ttgcaattag aaacaaatat cgtttacaaa gaggcaaaag aagctgtgga tgctttattt    2760
gtaaactctc aatatgatag attacaagtg gatacgaaca ttgccatgat tcatgcggca    2820
gataaacgcg ttcatagaat ccgagaagcg tatcttccag agttatctgt gattccgggt    2880
gtcaatgcgg ctattttcga agaattagaa gggtgtgttt tcactgcatt ctccctatat    2940
gatgcgagaa atgtcattaa aaatggcgat tttaataatg gcttatcatg ctggaacgtg    3000
aaagggcatg tagaagaaca aaacgaccat cgttcggtcc ttgttgtccc ggaatgggaa    3060
gcagaagtgt cacaagaggt tcgtgtctgt ccaggtcgtg gctatatcct tcgtgttaca    3120
gcatacaaag agggatatgg agaaggctgt gtaaccattc atgggatcga gaacaataca    3180
gacgaactga gtttagcaa ctgcgtagaa gaggaagtct atccaaacaa cacggtaacg    3240
tgtaatgatt atcctgcaaa tcaagaagaa tacggggtg cgtacacttc tcgtaatcgt    3300
ggatatgacg aaacttatgg aagcaattct tccgtatcag ctgattatgc gtcagtttat    3360
gaagaaaaag cgtatacaga tggacgaaga gacaatccat gtgaatttaa cagagggtat    3420
ggggattata cgccactacc agctggctat gtaacaaaag aattagaata cttcccagaa    3480
accgataagg tatggattga gattggagaa acggaaggaa cattcatcgt ggacagtgtg    3540
gaattactcc ttatggagga atag                                           3564
```

<210> SEQ ID NO 2
<211> LENGTH: 1187
<212> TYPE: PRT
<213> ORGANISM: Bacillus thuringienses
<220> FEATURE:
<221> NAME/KEY: MISC_FEATURE
<222> LOCATION: (1)..(1187)
<223> OTHER INFORMATION: The amino acid sequence of the TIC4472
      pesticidal protein.

<400> SEQUENCE: 2

```
Met Asn Asn Ile Glu Asn Gln Cys Val Pro Tyr Asn Cys Leu Ser
1               5                   10                  15

Asn Pro Glu Glu Val Ile Leu Asp Gly Glu Arg Ile Ser Thr Gly Asn
            20                  25                  30

Ser Ser Ile Asp Ile Ser Leu Ser Leu Val Gln Leu Leu Val Ser Asn
        35                  40                  45
```

-continued

```
Phe Val Pro Gly Gly Phe Leu Val Gly Leu Ile Asp Phe Val Trp
 50                  55                  60
Gly Ile Val Gly Pro Ser Pro Trp Asp Ala Phe Leu Val Gln Ile Glu
 65                  70                  75                  80
Gln Leu Ile Gln Gln Arg Ile Glu Ala Tyr Ala Arg Ala Ala Ile
                 85                  90                  95
Ser Asn Leu Glu Gly Ile Gly Asn Asn Phe Asn Ile Tyr Val Glu Ala
                100                 105                 110
Phe Gln Glu Trp Glu Glu Asp Pro Asn Asn Pro Ala Thr Arg Asn Arg
                115                 120                 125
Val Val Asp Arg Phe Arg Ile Leu Asp Gly Leu Leu Glu Arg Asp Ile
    130                 135                 140
Pro Ser Phe Arg Ile Ser Gly Phe Glu Val Pro Leu Leu Ser Val Tyr
145                 150                 155                 160
Ala Gln Ala Ala Asn Leu His Leu Ala Ile Leu Arg Asp Ser Val Ile
                165                 170                 175
Phe Gly Glu Arg Trp Gly Leu Thr Thr Thr Asn Val Asn Glu Asn Tyr
                180                 185                 190
Asn Arg Gln Ile Arg His Ile Asp Glu Tyr Ala Asp His Cys Ala Asn
                195                 200                 205
Thr Tyr Asn Arg Gly Leu Asn Asn Leu Pro Lys Ser Thr Tyr Gln Asp
    210                 215                 220
Trp Ile Thr Tyr Asn Arg Leu Arg Arg Glu Leu Thr Leu Thr Val Leu
225                 230                 235                 240
Asp Ile Ala Ala Phe Phe Pro Asn Tyr Asp Asn Arg Arg Tyr Pro Ile
                245                 250                 255
Gln Pro Val Gly Gln Leu Thr Arg Glu Val Tyr Thr Asp Pro Leu Ile
                260                 265                 270
Thr Phe Asn Pro Gln Leu Gln Ser Val Ala Gln Leu Pro Thr Phe Asn
                275                 280                 285
Val Met Glu Ser Asn Ala Ile Arg Asn Pro His Leu Phe Asp Ile Leu
    290                 295                 300
Asn Asn Leu Thr Ile Phe Thr Asp Trp Phe Ser Val Gly Arg Asn Phe
305                 310                 315                 320
Tyr Trp Gly Gly His Arg Val Thr Ser Asn Tyr Ile Gly Gly Gly Asn
                325                 330                 335
Ile Thr Ser Pro Ile Tyr Gly Arg Glu Ala Asn Gln Glu Pro Pro Arg
                340                 345                 350
Ser Phe Thr Phe Asn Gly Pro Val Phe Arg Thr Leu Ser Asn Pro Thr
                355                 360                 365
Leu Arg Leu Leu Gln Gln Pro Trp Pro Ala Pro Pro Phe Asn Leu Arg
    370                 375                 380
Gly Val Glu Gly Val Glu Phe Ser Thr Pro Thr Asn Ser Phe Thr Tyr
385                 390                 395                 400
Arg Gly Arg Gly Thr Val Asp Ser Leu Thr Glu Leu Pro Pro Glu Asp
                405                 410                 415
Asn Ser Val Leu Pro Arg Glu Gly Tyr Ser His Arg Leu Cys His Ala
                420                 425                 430
Thr Phe Val Gln Arg Ser Gly Thr Pro Phe Leu Thr Thr Gly Val Val
                435                 440                 445
Phe Ser Trp Thr His Arg Ser Ala Thr Leu Thr Asn Thr Ile Asp Pro
450                 455                 460
Asp Lys Ile Thr Gln Ile Pro Leu Val Lys Gly Phe Arg Val Trp Ser
```

```
                465                 470                 475                 480
Gly Ala Ser Val Val Thr Gly Pro Gly Phe Thr Gly Gly Asp Ile Leu
                    485                 490                 495
Arg Arg Thr Asn Phe Gly Asp Phe Val Ser Met Gln Val Asn Ile Asn
                500                 505                 510
Ser Pro Ile Thr Gln Arg Tyr Arg Leu Arg Phe Arg Tyr Ala Ser Ser
                515                 520                 525
Arg Asp Ala Arg Leu Thr Val Ala Thr Gly Ala Ala Asn Thr Gly Val
            530                 535                 540
Gly Gly Gln Ile Ser Val Asp Met Ala Leu Gln Lys Thr Met Glu Ile
545                 550                 555                 560
Gly Glu Ser Leu Thr Ser Arg Thr Phe Arg Tyr Thr Asp Phe Ser Asn
                    565                 570                 575
Pro Phe Ser Phe Arg Ala Asn Pro Asp Ile Ile Arg Ile Asn Glu Gln
                580                 585                 590
Pro Leu Phe Gly Ala Gly Ser Ile Ser Ser Gly Glu Leu Tyr Ile Asp
                595                 600                 605
Lys Ile Glu Ile Ile Leu Ala Asp Ala Thr Phe Glu Ala Glu Tyr Asp
            610                 615                 620
Leu Glu Arg Ala Gln Lys Ala Val Asn Ala Leu Phe Thr Ser Thr Asn
625                 630                 635                 640
Gln Arg Gly Leu Lys Thr Asp Val Thr Asp Tyr His Ile Asp Gln Val
                    645                 650                 655
Ser Asn Leu Val Glu Cys Leu Ser Asp Glu Phe Cys Leu Asp Glu Lys
                660                 665                 670
Arg Glu Leu Ser Glu Lys Val Lys His Ala Lys Arg Leu Ser Asp Glu
                675                 680                 685
Arg Asn Leu Leu Gln Asp Arg Asn Phe Thr Ser Ile Asn Gly Gln Leu
            690                 695                 700
Asp Arg Gly Trp Arg Gly Ser Thr Asp Ile Thr Ile Gln Gly Gly Asp
705                 710                 715                 720
Asp Val Phe Lys Glu Asn Tyr Val Thr Leu Leu Gly Thr Phe Asp Glu
                    725                 730                 735
Cys Tyr Pro Thr Tyr Leu Tyr Gln Lys Ile Asp Glu Ser Lys Leu Lys
                740                 745                 750
Ala Tyr Thr Arg Tyr Glu Leu Arg Gly Tyr Ile Glu Asp Ser Gln Asp
                755                 760                 765
Leu Glu Ile Tyr Leu Ile Arg Tyr Asn Ala Lys His Glu Thr Val Asn
            770                 775                 780
Val Pro Gly Thr Gly Ser Leu Trp Pro Leu Ser Val Glu Ser Pro Ile
785                 790                 795                 800
Gly Lys Cys Gly Glu Pro Asn Arg Cys Thr Pro His Leu Glu Trp Asn
                    805                 810                 815
Pro Asn Leu Asp Cys Ser Cys Arg Asp Gly Lys Thr Cys Ala His His
                820                 825                 830
Ser His His Phe Ser Leu Asp Ile Asp Val Gly Cys Thr Asp Leu Asn
                835                 840                 845
Glu Asp Leu Gly Val Trp Val Ile Phe Lys Ile Lys Thr Gln Asp Gly
            850                 855                 860
His Ala Arg Leu Gly Asn Leu Glu Phe Leu Glu Glu Lys Pro Leu Val
865                 870                 875                 880
Gly Glu Ala Leu Ala Arg Val Lys Arg Ala Glu Lys Lys Trp Arg Asp
                    885                 890                 895
```

```
Lys Arg Glu Lys Leu Gln Leu Glu Thr Asn Ile Val Tyr Lys Glu Ala
            900                 905                 910

Lys Glu Ala Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Cys Val Phe Thr Ala
                965                 970                 975

Phe Ser Leu Tyr Asp Ala Arg Asn Val Ile Lys Asn Gly Asp Phe Asn
            980                 985                 990

Asn Gly Leu Ser Cys Trp Asn Val  Lys Gly His Val Glu  Glu Gln Asn
        995                 1000                 1005

Asp His  Arg Ser Val Leu Val  Val Pro Glu Trp Glu  Ala Glu Val
    1010                 1015                 1020

Ser Gln  Glu Val Arg Val Cys  Pro Gly Arg Gly Tyr  Ile Leu Arg
    1025                 1030                 1035

Val Thr  Ala Tyr Lys Glu Gly  Tyr Gly Glu Gly Cys  Val Thr Ile
    1040                 1045                 1050

His Gly  Ile Glu Asn Asn Thr  Asp Glu Leu Lys Phe  Ser Asn Cys
    1055                 1060                 1065

Val Glu  Glu Glu Val Tyr Pro  Asn Asn Thr Val Thr  Cys Asn Asp
    1070                 1075                 1080

Tyr Pro  Ala Asn Gln Glu Glu  Tyr Gly Gly Ala Tyr  Thr Ser Arg
    1085                 1090                 1095

Asn Arg  Gly Tyr Asp Glu Thr  Tyr Gly Ser Asn Ser  Ser Val Ser
    1100                 1105                 1110

Ala Asp  Tyr Ala Ser Val Tyr  Glu Glu Lys Ala Tyr  Thr Asp Gly
    1115                 1120                 1125

Arg Arg  Asp Asn Pro Cys Glu  Phe Asn Arg Gly Tyr  Gly Asp Tyr
    1130                 1135                 1140

Thr Pro  Leu Pro Ala Gly Tyr  Val Thr Lys Glu Leu  Glu Tyr Phe
    1145                 1150                 1155

Pro Glu  Thr Asp Lys Val Trp  Ile Glu Ile Gly Glu  Thr Glu Gly
    1160                 1165                 1170

Thr Phe  Ile Val Asp Ser Val  Glu Leu Leu Leu Met  Glu Glu
    1175                 1180                 1185
```

<210> SEQ ID NO 3
<211> LENGTH: 3567
<212> TYPE: DNA
<213> ORGANISM: Artificial
<220> FEATURE:
<223> OTHER INFORMATION: A synthetic coding sequence encoding a TIC4472PL pesticidal protein designed for expression in a plant cell wherein an additional alanine codon is inserted immediately following the initiating methionine codon.

<400> SEQUENCE: 3

```
atggctaata acaacatcga gaaccagtgc gtgccctaca actgcctttc gaacccggag      60
gaagtgatcc tggacggcga aaggatctcg accgggaata gcagcatcga catctcgctt     120
tcgctcgtgc agcttctagt cagtaacttc gttccgggcg gagggtttct cgtgggcctt     180
attgacttcg tttggggcat cgtgggccca tctccttggg acgcattcct cgtgcagatc     240
```

```
gagcaactga tccagcagcg tatcgaggcg tacgctaggg ctgccgctat ctccaacctg    300
gagggcatcg gcaacaactt caacatctac gttgaagcct tccaagaatg ggaggaagat    360
cctaataacc cagctacgcg gaacagagtg gtggatcgct ttagaatcct cgacggcctc    420
ctggaaaggg acatcccgag cttccgtatt tccggcttcg aggtgccgct gctgagcgtg    480
tacgcgcaag cggccaatct gcacctggcg attctccggg actctgtgat cttcggcgag    540
cggtggggcc tcaccaccac taacgtgaac gagaactaca accgccagat ccgccacatc    600
gacgagtacg cggaccactg cgccaacaca tacaatcgcg ggctgaacaa cctccctaag    660
agcacttacc aagattggat cacctacaac aggctccgcc gggaactcac tctcacagtc    720
ctcgacatcg ctgccttctt cccgaactac gacaaccgcc gctacccgat tcagccagtc    780
ggccagctca cccgtgaggt gtacaccgat ccactgataa ctttcaatcc gcagctccag    840
tctgtcgcac agttgcccac cttcaacgtc atggaaagca cgccatcag gaacccacac    900 ttgttcgaca tccttaacaa cctgactatc ttcaccgact ggttcagcgt cggacggaac    960
ttctactggg gcggacaccg cgtcacctca aactacatcg gcggcggcaa cattacttcg    1020
cccatctacg gccgggaggc gaatcaggag ccgccacgca gctttacatt caacggtcct    1080
gtgtttcgca cgttatcgaa cccgacactc aggctgctcc agcagccctg gcctgcgccg    1140
ccgtttaatt tgcgcggcgt cgaaggcgtc gagttcagta cgccgaccaa cagcttcacc    1200
tatcgcggac gcgggactgt tgactccctg acagagctgc cgccggagga caactcggtt    1260
ctgccgcgtg agggctacag ccataggctt tgtcacgcga cctttgtgca gcgatccggg    1320
acaccgttcc ttacaaccgg cgtggtgttc tcctggacac accgcagtgc aactctgacg    1380
aacacgattg acccagacaa gatcacgcag atcccgttag tgaagggctt ccgggtttgg    1440
tctggtgcct ctgtagtcac tgggcctggc tttacgggtg gcgacatcct ccgtcgcacg    1500
aactttggcg acttcgtgtc catgcaagtg aacattaaca gccctattac gcaacgctac    1560
cggctgaggt tcagatacgc ttcctcgcgg gacgcccgtc ttacggtggc gacgggcgca    1620
gcgaacactg gagttggcgg ccaaatctcc gtggacatgg ctttgcagaa gactatggag    1680
atcggtgagt ctctcacatc tcgcacgttc cgctacacgg atttctccaa cccttttctcc    1740 ttccgcgcca atccggacat cattcggatc aacgaacagc cgctcttcgg cgcgggctcc    1800
atctcatccg gtgagctttta cattgataag attgagataa ttctggccga cgcgacctttt    1860 gaggcagagt atgatctgga gcgcgcacag aaggccgtga acgcgctgtt tacgtccacg    1920
aaccagcgcg ggctcaagac agacgtcaca gactaccaca tcgaccaagt ctccaacctt    1980
gtcgagtgtc tctccgacga gttctgcctg gacgagaagc gggagcttag tgagaaggtg    2040
aagcacgcaa agcgcctgtc tgacgagcgg aaccttctac aagaccgtaa cttcacctcc    2100
attaacgggc agctagaccg tggctggcgc gggtccaccg acatcactat ccaaggtggc    2160
gacgacgtct tcaaggagaa ctacgtgacg ctgctcggca cctttgacga gtgctacccg    2220
acatacctct atcagaagat tgacgagtct aagctcaagg cttacacccg ttacgagctg    2280
cgtggctaca tcgaggactc ccaggatctg gaaatctatc tcatcagata caacgcgaag    2340
cacgagacag tcaacgtacc tgggacaggc tctctctggc ctctgtctgt ggagagtccc    2400
atcggcaaat gtggcgagcc gaacagatgt actccgcacc tggagtggaa tcccaacttg    2460
gactgtagtt gccgcgacgg caagacctgc gcgcaccact cccaccactt ctccctggac    2520
attgacgtcg gctgcacgga tctcaacgag gatctgggcg tttgggtcat cttcaagata    2580
aagacccagg acggacacgc cagactggga aacctagagt tccttgagga gaagccgctg    2640
```

-continued

```
gtcggcgaag cactggcgcg ggtcaagagg gccgagaaga agtggcggga caaacgggag    2700
aaacttcaac tcgaaacgaa catcgtttac aaggaggcaa aggaggccgt ggacgcactg    2760
ttcgtgaact cgcagtacga ccgcctccaa gtggacacca acatcgccat gatccatgca    2820
gcggacaagc gcgtgcaccg aatcagggaa gcgtacttgc ccgagttgtc cgttatccct    2880
ggcgtgaacg ctgccatctt cgaggaactg gagggctgcg tgttcaccgc attctccctg    2940
tacgacgcac gaaacgtcat caagaatggc gacttcaaca acggcctgag ctgctggaac    3000
gtgaagggcc acgtggagga gcagaacgac caccgctccg tgttagtggt cccggaatgg    3060
gaagccgaag tgagccagga ggtcagggtg tgtcccggtc gcggttacat cctccgcgtg    3120
accgcctaca aggagggcta tggcgagggc tgcgtgacga tacacggtat cgagaacaac    3180
accgatgagc ttaagttctc gaactgcgtg gaggaggagg tgtacccgaa taacacagtg    3240
acgtgcaatg actacccggc caaccaggag gagtacggcg gtgcctacac gagccgaaac    3300
cgtggctatg acgaaactta cggctcgaac agcagcgtgt ctgcggatta tgccagtgtg    3360
tacgaggaga aggcgtacac ggacgggcgg cgcgacaacc cttgcgagtt caatagaggc    3420
tatggcgact acacgccgct gcccgccggt tatgtgacga aggagttgga atacttccca    3480
gagacggaca aggtgtggat cgagattggc gagaccgagg gcacgttcat gtggacagc    3540 gttgagctgc tactgatgga ggagtga    3567
```

<210> SEQ ID NO 4
<211> LENGTH: 1188
<212> TYPE: PRT
<213> ORGANISM: Artificial
<220> FEATURE:
<223> OTHER INFORMATION: The amino acid sequence of TIC4472PL encoded by a synthetic coding sequence designed for expression in a plant cell (SEQ ID NO:3), and wherein an additional alanine amino acid is inserted immediately following the initiating methionine.

<400> SEQUENCE: 4

```
Met Ala Asn Asn Ile Glu Asn Gln Cys Val Pro Tyr Asn Cys Leu
1               5                   10                  15

Ser Asn Pro Glu Glu Val Ile Leu Asp Gly Glu Arg Ile Ser Thr Gly
            20                  25                  30

Asn Ser Ser Ile Asp Ile Ser Leu Ser Leu Val Gln Leu Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Pro Trp Asp Ala Phe Leu Val Gln Ile
65                  70                  75                  80

Glu Gln Leu Ile Gln Gln Arg Ile Glu Ala Tyr Ala Arg Ala Ala Ala
                85                  90                  95

Ile Ser Asn Leu Glu Gly Ile Gly Asn Asn Phe Asn Ile Tyr Val Glu
                100                 105                 110

Ala Phe Gln Glu Trp Glu Glu Asp Pro Asn Asn Pro Ala Thr Arg Asn
            115                 120                 125

Arg Val Val Asp Arg Phe Arg Ile Leu Asp Gly Leu Leu Glu Arg Asp
        130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175
```

```
Ile Phe Gly Glu Arg Trp Gly Leu Thr Thr Asn Val Asn Glu Asn
            180                 185                 190

Tyr Asn Arg Gln Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Glu Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Thr Phe Asn Pro Gln Leu Gln Ser Val Ala Gln Leu Pro Thr Phe
        275                 280                 285

Asn Val Met Glu Ser Asn Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Thr Ser Asn Tyr Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Leu Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Asp Lys Ile Thr Gln Ile Pro Leu Val Lys Gly Phe Arg Val Trp
465                 470                 475                 480

Ser Gly Ala Ser Val Val Thr Gly Pro Gly Phe Thr Gly Gly Asp Ile
                485                 490                 495

Leu Arg Arg Thr Asn Phe Gly Asp Phe Val Ser Met Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Leu Thr Val Ala Thr Gly Ala Ala Asn Thr Gly
    530                 535                 540

Val Gly Gly Gln Ile Ser Val Asp Met Ala Leu Gln Lys Thr Met Glu
545                 550                 555                 560

Ile Gly Glu Ser Leu Thr Ser Arg Thr Phe Arg Tyr Thr Asp Phe Ser
                565                 570                 575

Asn Pro Phe Ser Phe Arg Ala Asn Pro Asp Ile Ile Arg Ile Asn Glu
            580                 585                 590

Gln Pro Leu Phe Gly Ala Gly Ser Ile Ser Ser Gly Glu Leu Tyr Ile
```

```
                    595                 600                 605
Asp Lys Ile Glu Ile Ile Leu Ala Asp Ala Thr Phe Glu Ala Glu Tyr
610                 615                 620

Asp Leu Glu Arg Ala Gln Lys Ala Val Asn Ala Leu Phe Thr Ser Thr
625                 630                 635                 640

Asn Gln Arg Gly Leu Lys Thr Asp Val Thr Asp Tyr His Ile Asp Gln
                645                 650                 655

Val Ser Asn Leu Val Glu Cys Leu Ser Asp Glu Phe Cys Leu Asp Glu
            660                 665                 670

Lys Arg Glu Leu Ser Glu Lys Val Lys His Ala Lys Arg Leu Ser Asp
        675                 680                 685

Glu Arg Asn Leu Leu Gln Asp Arg Asn Phe Thr Ser Ile Asn Gly Gln
    690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750

Lys Ala Tyr Thr Arg Tyr Glu Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Val Glu Ser Pro
785                 790                 795                 800

Ile Gly Lys Cys Gly Glu Pro Asn Arg Cys Thr Pro His Leu Glu Trp
                805                 810                 815

Asn Pro Asn Leu Asp Cys Ser Cys Arg Asp Gly Lys Thr Cys Ala His
            820                 825                 830

His Ser His His Phe Ser Leu Asp Ile Asp Val Gly Cys Thr Asp Leu
        835                 840                 845

Asn Glu Asp Leu Gly Val Trp Val Ile Phe Lys Ile Lys Thr Gln Asp
850                 855                 860

Gly His Ala Arg Leu Gly Asn Leu Glu Phe Leu Glu Glu Lys Pro Leu
865                 870                 875                 880

Val Gly Glu Ala Leu Ala Arg Val Lys Arg Ala Glu Lys Lys Trp Arg
                885                 890                 895

Asp Lys Arg Glu Lys Leu Gln Leu Glu Thr Asn Ile Val Tyr Lys Glu
            900                 905                 910

Ala Lys Glu Ala Val Asp Ala Leu Phe Val Asn Ser Gln Tyr Asp Arg
        915                 920                 925

Leu Gln Val Asp Thr Asn Ile Ala Met Ile His Ala Ala Asp Lys Arg
    930                 935                 940

Val His Arg Ile Arg Glu Ala Tyr Leu Pro Glu Leu Ser Val Ile Pro
945                 950                 955                 960

Gly Val Asn Ala Ala Ile Phe Glu Glu Leu Glu Gly Cys Val Phe Thr
                965                 970                 975

Ala Phe Ser Leu Tyr Asp Ala Arg Asn Val Ile Lys Asn Gly Asp Phe
            980                 985                 990

Asn Asn Gly Leu Ser Cys Trp Asn Val Lys Gly His Val Glu Glu Gln
        995                 1000                1005

Asn Asp His Arg Ser Val Leu Val Val Pro Glu Trp Glu Ala Glu
    1010                1015                1020
```

| | | | | | | | | | | |
|---|---|---|---|---|---|---|---|---|---|---|
| Val | Ser | Gln | Glu | Val | Arg | Val | Cys | Pro | Gly | Arg | Gly | Tyr | Ile | Leu |
| | 1025 | | | | 1030 | | | | 1035 | |

Arg Val Thr Ala Tyr Lys Glu Gly Tyr Gly Glu Gly Cys Val Thr
    1040                1045                1050

Ile His Gly Ile Glu Asn Asn Thr Asp Glu Leu Lys Phe Ser Asn
    1055                1060                1065

Cys Val Glu Glu Glu Val Tyr Pro Asn Asn Thr Val Thr Cys Asn
    1070                1075                1080

Asp Tyr Pro Ala Asn Gln Glu Glu Tyr Gly Gly Ala Tyr Thr Ser
    1085                1090                1095

Arg Asn Arg Gly Tyr Asp Glu Thr Tyr Gly Ser Asn Ser Ser Val
    1100                1105                1110

Ser Ala Asp Tyr Ala Ser Val Tyr Glu Glu Lys Ala Tyr Thr Asp
    1115                1120                1125

Gly Arg Arg Asp Asn Pro Cys Glu Phe Asn Arg Gly Tyr Gly Asp
    1130                1135                1140

Tyr Thr Pro Leu Pro Ala Gly Tyr Val Thr Lys Glu Leu Glu Tyr
    1145                1150                1155

Phe Pro Glu Thr Asp Lys Val Trp Ile Glu Ile Gly Glu Thr Glu
    1160                1165                1170

Gly Thr Phe Ile Val Asp Ser Val Glu Leu Leu Leu Met Glu Glu
    1175                1180                1185

<210> SEQ ID NO 5
<211> LENGTH: 3564
<212> TYPE: DNA
<213> ORGANISM: Bacillus thuringienses
<220> FEATURE:
<221> NAME/KEY: misc_feature
<222> LOCATION: (1)..(3564)
<223> OTHER INFORMATION: Nucleic acid sequence encoding a TIC1425
      pesticidal protein obtained from Bacillus thuringiensis species
      EG10731.

<400> SEQUENCE: 5
atgaataata atattgaaaa ccaatgcgta ccttacaatt gtttaagtaa tcctgaagaa     60
gtaattttgg atggagaacg gatatcaact ggtaattcat caattgatat ttctctgtca    120
cttgttcaac ttctggtatc taactttgta ccaggcggag gattttttagt agggttaata    180 gattttgtat ggggaatagt aggcccttct ccatgggatg catttctagt gcaaattgaa    240
caattaattc agcaaagaat agaagcatat gctagggctg cagcaatttc taatttagaa    300
ggaataggaa acaatttcaa tatatatgtg gaagcatttc aagaatggga agaagatcct    360
aataatccag caaccaggaa tagagtagtt gatcgctttc gtatacttga tgggctactt    420
gaaagggaca ttccttcgtt tcgaatttct ggatttgaag tccccctttt atccgtttat    480
gctcaagcgg ccaatctgca tctagctata ttaagagatt ctgtaatttt tggagaaaga    540
tggggattga caacaacaaa tgtcaatgaa actataata gacaaatcag gcatattgat    600
gaatatgctg atcactgtgc aaatacgtat aatcggggat taaataattt accgaaatct    660
acgtatcaag attggataac atataatcga ttacggagag aattaacatt gactgtatta    720
gatatcgctg ctttctttcc aaactatgac aataggcggt atccaattca gccagttggt    780
caactaacaa gggaagttta tacggaccca ttaattactt ttaatcccca gttacagtct    840
gtagctcaat tacctacttt taacgttatg gaaagcaacg caattagaaa tcctcatttg    900
tttgatatat tgaataatct tacaattttt acggattggt ttagtgttgg acgcaacttt    960

-continued

```
tattggggag gacatcgagt aacttctaac tatataggag gaggcaacat aacatctcct      1020
atatatggaa gagaggcgaa ccaggagcct ccaagatctt ttacttttaa tggacctgtt      1080
tttaggactt tatcaaatcc tactttacga ttattacagc aaccttggcc agcaccacca      1140
tttaatttac gtggtgttga aggagtgaaa ttttctacac ctacaaatag ctttacgtat      1200
cgaggaagag gtacagttga ttctttaacc gaattaccgc ctgaggataa tagtgtgcta      1260
cctcgcgagg gatatagtca tcgtttatgt catgcaactt tgttcaaag atctggaaca      1320 ccattttaa caacgggtgt agtattttct tggacgcatc gcagtgcaac tcttacaaat      1380
acaattgatc cagacaaaat tactcagata cctttagtga aaggatttag agtttggagt      1440
ggcgcctctg tcgttacagg accaggtttt acaggagggg atatccttcg aagaactaac      1500
tttggggatt ttgtatctat gcaagttaat attaattcac caataacaca aagataccgt      1560
ttaagatttc gttatgcttc cagtagagat gcacgactta cagtagcgac aggagcagca      1620
aacacaggag ttggagggca aattagtgtg gacatggctc ttcagaaaac tatggaaatt      1680
ggagagagct taacatctag aacatttaga tataccgatt ttagtaatcc ttttcatt      1740 agagctaatc cagatataat tcgtataaat gaacaaccac tattcggtgc aggctctatt      1800
agtagtggtg aactttatat agataaaatt gaaattattc tagcagatgc aacatttgaa      1860
gcagaatatg atttggaaag agcacagaag gcggtgaatg cgctgtttac ttctacaaac      1920
caaagaggat taaaaacaga tgtgacggat tatcatattg atcaagtatc caatttagtt      1980
gagtgtttat cggatgaatt ttgtctggat gaaaaacgag aattgtccga gaaagtcaaa      2040
catgcgaagc gactcagtga tgagcgaaat ttactccagg atcgaaattt cacatccatt      2100
aatgggcaac tagaccgtgg ctggagagga agtacggata ttaccatcca aggaggagat      2160
gacgtattca aagagaatta cgtcacacta ctgggtacct tgatgagtg ctatccaacg      2220 tatttatatc aaaaaataga tgagtcgaaa ttaaaagcct atacccgcta tgaattaaga      2280
gggtatatcg aggatagtca agacttagaa atctatttaa ttcgctacaa tgcaaaacac      2340
gaaacagtaa atgtgccagg tacaggttcc ttatggccgc tttcagtcga agtccaatc      2400 ggaaagtgtg gagaaccgaa tcgatgcaca ccacaccttg aatggaatcc taatctagat      2460
tgttcctgca gagacgggaa aacatgtgca catcattctc atcatttctc cttggacatt      2520
gatgttggat gtacagactt aaatgaagat ctaggtgtat gggtgatatt caagattaag      2580
acgcaagatg gtcatgcaag actaggaaat ctagagtttc tcgaagagaa accattagta      2640
ggagaagcgt tagctcgtgt gaaaagagcg gagaaaaaat ggagagacaa acgcgaaaaa      2700
ttgcaattag aaacaaatat cgtttacaaa gaggcaaaag aagctgtgga tgctttattt      2760
gtaaactctc aatatgatag attacaagtg gatacgaaca ttgccatgat tcatgcggca      2820
gataaacgcg ttcatagaat ccgagaagcg tatcttccag agttatctgt gattccgggt      2880
gtcaatgcgg ctatttttcga agaattagaa gggtgtattt tcactgcatt ctccctatat      2940
gatgcgagaa atgtcattaa aaatggcgat tttaataatg gcttatcatg ctggaacgtg      3000
aaagggcatg tagaagaaca aaacgaccat cgttcggtcc ttgttgtccc ggaatgggaa      3060
gcagaagtgt cacaagaggt tcgtgtctgt ccaggtcgtg gctatatcct tcgtgttaca      3120
gcatacaaag agggatatgg agaaggctgt gtaaccattc atgggatcga gaacaataca      3180
gacgaactga gtttagcaa ctgcgtagaa gaggaagtct atccaaacaa cacggtaacg      3240
tgtaatgatt atcctgcaaa tcaagaagaa tacgggggtg cgtacacttc tcgtaatcgt      3300
```

-continued

```
ggatatgacg aaacttatgg aagcaattct tccgtatcag ctgattatgc gtcagtttat    3360
gaagaaaaag cgtatacaga tggacgaaga gacaatccat gtgaatttaa cagagggtat    3420
ggggattata cgccactacc agctggctat gtaacaaaag aattagaata cttcccagaa    3480
accgataagg tatggattga gattggagaa acggaaggaa cattcatcgt ggacagtgtg    3540
gaattactcc ttatggagga ataa                                          3564
```

<210> SEQ ID NO 6
<211> LENGTH: 1187
<212> TYPE: PRT
<213> ORGANISM: Bacillus thuringienses
<220> FEATURE:
<221> NAME/KEY: MISC_FEATURE
<222> LOCATION: (1)..(1187)
<223> OTHER INFORMATION: The amino acid sequence of the TIC1425 pesticidal protein.

<400> SEQUENCE: 6

```
Met Asn Asn Ile Glu Asn Gln Cys Val Pro Tyr Asn Cys Leu Ser
1               5                   10                  15

Asn Pro Glu Glu Val Ile Leu Asp Gly Glu Arg Ile Ser Thr Gly Asn
            20                  25                  30

Ser Ser Ile Asp Ile Ser Leu Ser Leu Val Gln Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Pro Trp Asp Ala Phe Leu Val Gln Ile Glu
65                  70                  75                  80

Gln Leu Ile Gln Gln Arg Ile Glu Ala Tyr Ala Arg Ala Ala Ile
                85                  90                  95

Ser Asn Leu Glu Gly Ile Gly Asn Asn Phe Asn Ile Tyr Val Glu Ala
            100                 105                 110

Phe Gln Glu Trp Glu Glu Asp Pro Asn Asn Pro Ala Thr Arg Asn Arg
        115                 120                 125

Val Val Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Thr Asn Val Asn Glu Asn Tyr
            180                 185                 190

Asn Arg Gln Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Glu Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Thr Phe Asn Pro Gln Leu Gln Ser Val Ala Gln Leu Pro Thr Phe Asn
        275                 280                 285

Val Met Glu Ser Asn Ala Ile Arg Asn Pro His Leu Phe Asp Ile Leu
    290                 295                 300
```

```
Asn Asn Leu Thr Ile Phe Thr Asp Trp Phe Ser Val Gly Arg Asn Phe
305                 310                 315                 320

Tyr Trp Gly Gly His Arg Val Thr Ser Asn Tyr Ile Gly Gly Asn
            325                 330                 335

Ile Thr Ser Pro Ile Tyr Gly Arg Glu Ala Asn Gln Glu Pro Pro Arg
                340                 345                 350

Ser Phe Thr Phe Asn Gly Pro Val Phe Arg Thr Leu Ser Asn Pro Thr
            355                 360                 365

Leu Arg Leu Leu Gln Gln Pro Trp Pro Ala Pro Pro Phe Asn Leu Arg
            370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Leu Pro Arg Glu Gly Tyr Ser His Arg Leu Cys His Ala
            420                 425                 430

Thr Phe Val Gln Arg Ser Gly Thr Pro Phe Leu Thr Thr Gly Val Val
            435                 440                 445

Phe Ser Trp Thr His Arg Ser Ala Thr Leu Thr Asn Thr Ile Asp Pro
450                 455                 460

Asp Lys Ile Thr Gln Ile Pro Leu Val Lys Gly Phe Arg Val Trp Ser
465                 470                 475                 480

Gly Ala Ser Val Val Thr Gly Pro Gly Phe Thr Gly Gly Asp Ile Leu
                485                 490                 495

Arg Arg Thr Asn Phe Gly Asp Phe Val Ser Met Gln Val Asn Ile Asn
            500                 505                 510

Ser Pro Ile Thr Gln Arg Tyr Arg Leu Arg Phe Arg Tyr Ala Ser Ser
            515                 520                 525

Arg Asp Ala Arg Leu Thr Val Ala Thr Gly Ala Ala Asn Thr Gly Val
            530                 535                 540

Gly Gly Gln Ile Ser Val Asp Met Ala Leu Gln Lys Thr Met Glu Ile
545                 550                 555                 560

Gly Glu Ser Leu Thr Ser Arg Thr Phe Arg Tyr Thr Asp Phe Ser Asn
                565                 570                 575

Pro Phe Ser Phe Arg Ala Asn Pro Asp Ile Ile Arg Ile Asn Glu Gln
            580                 585                 590

Pro Leu Phe Gly Ala Gly Ser Ile Ser Ser Gly Glu Leu Tyr Ile Asp
            595                 600                 605

Lys Ile Glu Ile Ile Leu Ala Asp Ala Thr Phe Glu Ala Glu Tyr Asp
            610                 615                 620

Leu Glu Arg Ala Gln Lys Ala Val Asn Ala Leu Phe Thr Ser Thr Asn
625                 630                 635                 640

Gln Arg Gly Leu Lys Thr Asp Val Thr Asp Tyr His Ile Asp Gln Val
                645                 650                 655

Ser Asn Leu Val Glu Cys Leu Ser Asp Glu Phe Cys Leu Asp Glu Lys
            660                 665                 670

Arg Glu Leu Ser Glu Lys Val Lys His Ala Lys Arg Leu Ser Asp Glu
            675                 680                 685

Arg Asn Leu Leu Gln Asp Arg Asn Phe Thr Ser Ile Asn Gly Gln Leu
            690                 695                 700

Asp Arg Gly Trp Arg Gly Ser Thr Asp Ile Thr Ile Gln Gly Gly Asp
705                 710                 715                 720
```

-continued

```
Asp Val Phe Lys Glu Asn Tyr Val Thr Leu Gly Thr Phe Asp Glu
            725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
            755                 760                 765

Leu Glu Ile Tyr Leu Ile Arg Tyr Asn Ala Lys His Glu Thr Val Asn
            770                 775                 780

Val Pro Gly Thr Gly Ser Leu Trp Pro Leu Ser Val Glu Ser Pro Ile
785                 790                 795                 800

Gly Lys Cys Gly Glu Pro Asn Arg Cys Thr Pro His Leu Glu Trp Asn
            805                 810                 815

Pro Asn Leu Asp Cys Ser Cys Arg Asp Gly Lys Thr Cys Ala His His
            820                 825                 830

Ser His His Phe Ser Leu Asp Ile Asp Val Gly Cys Thr Asp Leu Asn
            835                 840                 845

Glu Asp Leu Gly Val Trp Val Ile Phe Lys Ile Lys Thr Gln Asp Gly
            850                 855                 860

His Ala Arg Leu Gly Asn Leu Glu Phe Leu Glu Lys Pro Leu Val
865                 870                 875                 880

Gly Glu Ala Leu Ala Arg Val Lys Arg Ala Glu Lys Lys Trp Arg Asp
            885                 890                 895

Lys Arg Glu Lys Leu Gln Leu Glu Thr Asn Ile Val Tyr Lys Glu Ala
            900                 905                 910

Lys Glu Ala Val Asp Ala Leu Phe Val Asn Ser Gln Tyr Asp Arg Leu
            915                 920                 925

Gln Val Asp Thr Asn Ile Ala Met Ile His Ala Ala Asp Lys Arg Val
            930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Cys Ile Phe Thr Ala
            965                 970                 975

Phe Ser Leu Tyr Asp Ala Arg Asn Val Ile Lys Asn Gly Asp Phe Asn
            980                 985                 990

Asn Gly Leu Ser Cys Trp Asn Val Lys Gly His Val Glu Glu Gln Asn
            995                 1000                1005

Asp His Arg Ser Val Leu Val Val Pro Glu Trp Glu Ala Glu Val
            1010                1015                1020

Ser Gln Glu Val Arg Val Cys Pro Gly Arg Gly Tyr Ile Leu Arg
            1025                1030                1035

Val Thr Ala Tyr Lys Glu Gly Tyr Gly Glu Gly Cys Val Thr Ile
            1040                1045                1050

His Gly Ile Glu Asn Asn Thr Asp Glu Leu Lys Phe Ser Asn Cys
            1055                1060                1065

Val Glu Glu Glu Val Tyr Pro Asn Asn Thr Val Thr Cys Asn Asp
            1070                1075                1080

Tyr Pro Ala Asn Gln Glu Glu Tyr Gly Gly Ala Tyr Thr Ser Arg
            1085                1090                1095

Asn Arg Gly Tyr Asp Glu Thr Tyr Gly Ser Asn Ser Ser Val Ser
            1100                1105                1110

Ala Asp Tyr Ala Ser Val Tyr Glu Glu Lys Ala Tyr Thr Asp Gly
            1115                1120                1125

Arg Arg Asp Asn Pro Cys Glu Phe Asn Arg Gly Tyr Gly Asp Tyr
```

```
                1130                1135                1140
Thr Pro Leu Pro Ala Gly Tyr Val Thr Lys Glu Leu Glu Tyr Phe
        1145                1150                1155
Pro Glu Thr Asp Lys Val Trp Ile Glu Ile Gly Glu Thr Glu Gly
        1160                1165                1170
Thr Phe Ile Val Asp Ser Val Glu Leu Leu Leu Met Glu Glu
        1175                1180                1185

<210> SEQ ID NO 7
<211> LENGTH: 3537
<212> TYPE: DNA
<213> ORGANISM: Bacillus thuringienses
<220> FEATURE:
<221> NAME/KEY: misc_feature
<222> LOCATION: (1)..(3537)
<223> OTHER INFORMATION: Nucleic acid sequence encoding a TIC2613
      pesticidal protein obtained from Bacillus thuringiensis species
      EG5408.

<400> SEQUENCE: 7
atggataaca atatcaagaa ccaatgcatt ccttacaatt gtttaaatga tcctgaggta      60
gaaatattag gtgaagaggg gataaactact agtaatgaaa atctcgaatt tttcttatcg     120
```

```
agggccgtaa atcaggctaa tttcccagca actatgaata gagtagaaga cttagaatat    1680 aattcccttta gaacgataag tttcggtact cctttttaact ttttagatgc tcaaagtacc  1740
ttcaggttag gtgtatggag cttttcttca ggtaccgttt taatagatag aattgaagtt   1800
gtaccaatgg aagtaacatt tgaagcagaa tctgatttag aaagagcaca aaggcggtg    1860 aacgctctgt ttacttctat aaatcaaaaa ggactaaaaa cagatgtaac agattatcac   1920
attgatcaag tatccaattt ggtcgaatgt ctatccgatg aattttgtct agatgaaaag   1980
agagaactat ttgagaaagt caaatatgcg aaacgactca gtgacgaacg gaatttactt   2040
gcagatccaa atttcacatc tattaatggg caactagatc gtggatggag aggaagtacg   2100
gatattacca ttcaaggggg cgatgacgta ttcaaagaaa actacgtcac actatcaggt   2160
acccttgatg agtgttatcc aacctattta tatcaaaaaa tagacgaatc gaaattaaaa   2220
gcgtataccc gttacgagtt acgaggatat atcgaagata gtcaagattt agaagtatac   2280
ttgattcgtt acaataccaa acatgaaaca ttgaatgtac caggtacagg gggcctatgg   2340
ccgcttgcag tagaaagttc aatcggaggg tgtggcgaac caaaccgatg cgcaccacaa   2400
atggaatggg atccaaatct agaatgttct tgtagcgacg aggagaaatg tgcgcatcat   2460
tcccatcatt tctctctcga tattgatgtt ggatgtactg atttaaatga aaatctaggt   2520
atatgggtta tatttaaaat taaaacgcag aacggttatg caaaattagg aaatttagag   2580
tttctcgaag agaaaccatt aataggggaa gcgttagctc gtgttaagcg agtggagaaa   2640
aaatggaaag acaaacgtga aaaattagaa tttgaaacga atatagtcta caacgaggca   2700
aaagaagctg tggatgcact attcgtaaat tcacaatatg atagattgca agctgataca   2760
aatatcgcaa tgattcatgc ggcggataac aaagttcata aaattcgcga ggcgtacctc   2820
ccagagttat ctgtgatacc aggtgtaaat gcgaccgttt ttgaagaatt agaagagcgt   2880
atttttacag cattctcccct ttacgatgca agaaatgtga taaaaaatgg ggatttcaat   2940 aatgattat cttgttggaa tgtgaagggc caagtagatg tagaccaaaa tgaccatcgt   3000
tctgtccttg ttattccagg atgggaatcg gaagtatcac aagaagttca tgtatgtcca   3060
gatcgtggat acattcttcg tgttacggcg tacaaagaag gatatggaga aggctgcgta   3120
acaatccatg agattgataa tcatacagac gaactgaaat ttaaaaactg ctttgaagag   3180
gaagtatctc taaataatgc ggtgacatgt gatgagtata ctacaaatca agaagtagga   3240
gggtatgcgg atgtacgtca atccaataat cgtggatcta atgaggccta tgtaaatcct   3300
acttccacat caactgatta tgcatcgctc tacgaggaag agtcgtatac gaatgaacag   3360
acatataatt cttgtgaatc taacagaggg tatggtaatc aaatgccatt accgtctggc   3420
tatgtgacaa aagaattaga atattttcca gagacagata agtatggat tgagattgga   3480 gaaacagaag gaacattcat cgtagacagt gtggaattac tccttatgga ggaataa     3537
```

<210> SEQ ID NO 8
<211> LENGTH: 1178
<212> TYPE: PRT
<213> ORGANISM: Bacillus thuringienses
<220> FEATURE:
<221> NAME/KEY: MISC_FEATURE
<222> LOCATION: (1)..(1178)
<223> OTHER INFORMATION: The amino acid sequence of the TIC2613
      pesticidal protein.

<400> SEQUENCE: 8

Met Asp Asn Asn Ile Lys Asn Gln Cys Ile Pro Tyr Asn Cys Leu Asn
1               5                   10                  15

```
Asp Pro Glu Val Glu Ile Leu Gly Glu Gly Ile Thr Thr Ser Asn
             20                  25                  30

Glu Asn Leu Glu Phe Phe Leu Ser Leu Thr Lys Phe Val Leu Asn Arg
         35                  40                  45

Phe Val Pro Gly Gly Ala Tyr Val Ala Gly Leu Phe Asp Val Phe Trp
 50                  55                  60

Gly Trp Leu Lys Pro Ser Asp Trp Ser Ala Ile Leu Glu Gln Ile Glu
 65                  70                  75                  80

Glu Leu Ile Asn Gln Lys Ile Glu Thr Phe Ala Arg Asn Gln Ala Ile
             85                  90                  95

Ser Arg Leu Glu Gly Leu Ser Asn Leu Tyr Glu Ile Tyr Ala Asp Thr
         100                 105                 110

Phe Lys Glu Trp Glu Lys Asp Pro Thr Asn Pro Ala Leu Arg Glu Glu
         115                 120                 125

Met Arg Thr Gln Phe Asn Asp Met Asn Ser Ser Phe Val Thr Ala Met
130                 135                 140

Pro Leu Phe Ser Val Gln Asn Phe Glu Val Pro Leu Leu Ala Val Tyr
145                 150                 155                 160

Ala Gln Ala Ala Asn Leu His Leu Ser Val Leu Arg Asp Val Ser Val
             165                 170                 175

Phe Gly Gln Asn Trp Gly Phe Asp Ser Ala Thr Val Asn Ser Arg Tyr
         180                 185                 190

Asn Asp Leu Val Arg Asn Ile Arg Thr Tyr Thr Asn Tyr Val Val Arg
         195                 200                 205

Trp Tyr Asn Thr Gly Leu Ala Arg Leu Arg Gly Thr Thr Tyr Gln Asp
210                 215                 220

Trp Leu Asn Tyr His Arg Phe Arg Arg Glu Leu Thr Ile Thr Ala Leu
225                 230                 235                 240

Asp Ile Ile Thr Ile Phe Pro His Tyr Asp Asn Lys Met Tyr Pro Ile
             245                 250                 255

Gln Pro His Phe Gln Leu Thr Arg Glu Ile Tyr Thr Asp Pro Leu Ile
         260                 265                 270

Asn Phe Asn Pro Ala Leu Gln Ser Val Ala Gln Leu Pro Leu Phe Asn
         275                 280                 285

Glu Met Glu Asn Ser Thr Ile Arg Ser Pro His Leu Val Asp Phe Leu
290                 295                 300

Asn Arg Leu Thr Ile Tyr Thr Asp Trp Tyr Ser Leu Gly Arg His Tyr
305                 310                 315                 320

Tyr Trp Gly Gly His Gln Ile Val Ser Arg Gln Thr Gly Ser Thr Ser
             325                 330                 335

Thr Ile Thr Phe Pro Ile Tyr Gly Arg Glu Ala Asn Gln Glu Ala Pro
         340                 345                 350

Arg Thr Tyr Asn Phe Ser Gln Pro Val Phe Arg Thr Leu Ser Asn Pro
         355                 360                 365

Thr Leu Thr Arg Leu Met Gln Pro Trp Pro Ala Pro Ala Phe Gln Leu
370                 375                 380

Arg Arg Leu Glu Gly Val Glu Phe Gln Thr Thr Thr Gly Asn Phe Thr
385                 390                 395                 400

Tyr Arg Gly Arg Gly Thr Val Asp Ser Phe Asp Glu Leu Pro Pro Asp
             405                 410                 415

Asp Thr Ser Val Pro Ala Arg Glu Gly Tyr Ser His Arg Leu Cys His
         420                 425                 430
```

-continued

Ala Thr Phe Ile Arg Lys Ser Gly Thr Pro Tyr Leu Thr Gly Val
        435                 440                 445

Thr Leu Ser Trp Thr His Asn Ser Asn Thr Pro Thr Asn Ile Ile Tyr
    450                 455                 460

Pro Asp Lys Ile Thr Gln Val Pro Leu Val Lys Ala Ser Asn Leu His
465                 470                 475                 480

Ser Ser Ala Phe Val Leu Lys Gly Pro Gly Phe Thr Gly Asp Ile
                485                 490                 495

Leu Gly Arg Thr Ser Val Gly Asn Ile Ala Asp Ile Gln Met Asn Ile
            500                 505                 510

Thr Ala Pro Leu Ser Gln Arg Tyr Arg Val Arg Ile Arg Tyr Ala Ser
            515                 520                 525

Thr Thr Asn Leu Gln Phe His Thr Thr Ile Asn Gly Arg Ala Val Asn
    530                 535                 540

Gln Ala Asn Phe Pro Ala Thr Met Asn Arg Val Glu Asp Leu Glu Tyr
545                 550                 555                 560

Asn Ser Phe Arg Thr Ile Ser Phe Gly Thr Pro Phe Asn Phe Leu Asp
                565                 570                 575

Ala Gln Ser Thr Phe Arg Leu Gly Val Trp Ser Phe Ser Ser Gly Thr
            580                 585                 590

Val Leu Ile Asp Arg Ile Glu Val Val Pro Met Glu Val Thr Phe Glu
            595                 600                 605

Ala Glu Ser Asp Leu Glu Arg Ala Gln Lys Ala Val Asn Ala Leu Phe
            610                 615                 620

Thr Ser Ile Asn Gln Lys Gly Leu Lys Thr Asp Val Thr Asp Tyr His
625                 630                 635                 640

Ile Asp Gln Val Ser Asn Leu Val Glu Cys Leu Ser Asp Glu Phe Cys
                645                 650                 655

Leu Asp Glu Lys Arg Glu Leu Phe Glu Lys Val Lys Tyr Ala Lys Arg
            660                 665                 670

Leu Ser Asp Glu Arg Asn Leu Leu Ala Asp Pro Asn Phe Thr Ser Ile
            675                 680                 685

Asn Gly Gln Leu Asp Arg Gly Trp Arg Gly Ser Thr Asp Ile Thr Ile
690                 695                 700

Gln Gly Gly Asp Asp Val Phe Lys Glu Asn Tyr Val Thr Leu Ser Gly
705                 710                 715                 720

Thr Leu Asp Glu Cys Tyr Pro Thr Tyr Leu Tyr Gln Lys Ile Asp Glu
                725                 730                 735

Ser Lys Leu Lys Ala Tyr Thr Arg Tyr Glu Leu Arg Gly Tyr Ile Glu
            740                 745                 750

Asp Ser Gln Asp Leu Glu Val Tyr Leu Ile Arg Tyr Asn Thr Lys His
            755                 760                 765

Glu Thr Leu Asn Val Pro Gly Thr Gly Leu Trp Pro Leu Ala Val
            770                 775                 780

Glu Ser Ser Ile Gly Gly Cys Gly Glu Pro Asn Arg Cys Ala Pro Gln
785                 790                 795                 800

Met Glu Trp Asp Pro Asn Leu Glu Cys Ser Cys Ser Asp Glu Lys
                805                 810                 815

Cys Ala His His Ser His His Phe Ser Leu Asp Ile Asp Val Gly Cys
            820                 825                 830

Thr Asp Leu Asn Glu Asn Leu Gly Ile Trp Val Ile Phe Lys Ile Lys
            835                 840                 845

Thr Gln Asn Gly Tyr Ala Lys Leu Gly Asn Leu Glu Phe Leu Glu Glu

```
                        850                 855                 860
Lys Pro Leu Ile Gly Glu Ala Leu Ala Arg Val Lys Arg Val Glu Lys
865                 870                 875                 880

Lys Trp Lys Asp Lys Arg Glu Lys Leu Glu Phe Glu Thr Asn Ile Val
                    885                 890                 895

Tyr Asn Glu Ala Lys Glu Ala Val Asp Ala Leu Phe Val Asn Ser Gln
                900                 905                 910

Tyr Asp Arg Leu Gln Ala Asp Thr Asn Ile Ala Met Ile His Ala Ala
            915                 920                 925

Asp Asn Lys Val His Lys Ile Arg Glu Ala Tyr Leu Pro Glu Leu Ser
        930                 935                 940

Val Ile Pro Gly Val Asn Ala Thr Val Phe Glu Glu Leu Glu Glu Arg
945                 950                 955                 960

Ile Phe Thr Ala Phe Ser Leu Tyr Asp Ala Arg Asn Val Ile Lys Asn
                965                 970                 975

Gly Asp Phe Asn Asn Gly Leu Ser Cys Trp Asn Val Lys Gly Gln Val
                980                 985                 990

Asp Val Asp Gln Asn Asp His Arg  Ser Val Leu Val Ile  Pro Gly Trp
        995                 1000                1005

Glu Ser  Glu Val Ser Gln Glu  Val His Val Cys Pro  Asp Arg Gly
    1010                1015                1020

Tyr Ile  Leu Arg Val Thr Ala  Tyr Lys Glu Gly Tyr  Gly Glu Gly
    1025                1030                1035

Cys Val  Thr Ile His Glu Ile  Asp Asn His Thr Asp  Glu Leu Lys
    1040                1045                1050

Phe Lys  Asn Cys Phe Glu Glu  Glu Val Ser Leu Asn  Asn Ala Val
    1055                1060                1065

Thr Cys  Asp Glu Tyr Thr Thr  Asn Gln Glu Val Gly  Gly Tyr Ala
    1070                1075                1080

Asp Val  Arg Gln Ser Asn Asn  Arg Gly Ser Asn Glu  Ala Tyr Val
    1085                1090                1095

Asn Pro  Thr Ser Thr Ser Thr  Asp Tyr Ala Ser Leu  Tyr Glu Glu
    1100                1105                1110

Glu Ser  Tyr Thr Asn Glu Gln  Thr Tyr Asn Ser Cys  Glu Ser Asn
    1115                1120                1125

Arg Gly  Tyr Gly Asn Gln Met  Pro Leu Pro Ser Gly  Tyr Val Thr
    1130                1135                1140

Lys Glu  Leu Glu Tyr Phe Pro  Glu Thr Asp Lys Val  Trp Ile Glu
    1145                1150                1155

Ile Gly  Glu Thr Glu Gly Thr  Phe Ile Val Asp Ser  Val Glu Leu
    1160                1165                1170

Leu Leu  Met Glu Glu
    1175

<210> SEQ ID NO 9
<211> LENGTH: 3540
<212> TYPE: DNA
<213> ORGANISM: Artificial
<220> FEATURE:
<223> OTHER INFORMATION: A synthetic coding sequence encoding a
      TIC2613PL pesticidal protein designed for expression in a plant
      cell wherein an additional alanine codon is inserted immediately
      following the initiating methionine codon.

<400> SEQUENCE: 9
atggctgaca caacatcaa gaaccagtgc atcccgtaca actgcctcaa cgacccggag      60
```

```
gtcgagatcc tcggcgagga gggcataacg acgagcaacg agaaccttga gttcttcctc    120
agcctcacga agttcgtcct gaaccgcttc gtgccgggcg agcctacgt ggctggcctg    180 ttcgatgtgt tctggggatg gctcaagcca agcgactggt ccgcgattct ggagcagatc    240
gaggaactca tcaaccagaa gatcgagaca ttcgcccgca accaggccat cagccgcctg    300
gagggcctct cgaacctcta cgaaatctac gccgatacgt tcaaggagtg ggagaaggat    360
ccgacgaacc cggccttgcg cgaggagatg aggacgcaat tcaacgacat gaactccagc    420
ttcgtcaccg ccatgccgct gttctccgtc cagaacttcg aggtgcccct gctcgccgtg    480
tacgcgcaag ctgcgaactt acatcttagc gtcctccgcg acgtcagcgt cttcggccag    540
aactggggat tcgattccgc gacggtgaac tcacggtaca atgatctcgt gcggaacatc    600
cggacctaca ccaattacgt cgtgcgctgg tacaacacgg gattggcgcg tctgcgcggc    660
actacctacc aggactggct caactaccac cggttccgcc gcgaactcac aatcacagcg    720
ctggacatca ttaccatctt cccgcactac gacaacaaga tgtacccaat ccagcctcac    780
ttccagctta cccgtgagat ctacacggac ccgctcatca acttcaatcc cgcactgcaa    840
tcagtagccc aattgccact cttcaacgag atggagaact cgacaatccg aagccctcac    900
ctcgtggact tcctcaaccg cctgaccatc tacacggatt ggtactctct tggtcggcac    960
tactattggg gcgggcacca aatcgtgtcc aggcagaccg gctctacctc taccataacc   1020
ttcccgatct atggccggga ggccaaccag gaggctccga ggacttacaa cttcagtcag   1080
ccagtgttcc gcacactctc caacccgact ctcactcgtt tgatgcagcc ctggcccgct   1140
cccgcgtttc agctcagaag attggagggc gtggagttcc aaacaacgac gggcaacttc   1200
acctaccgtg gccgtgggac ggtggacagt ttcgacgagt tgcctccgga cgacaccagc   1260
gtgcctgcaa gggaaggcta ctcgcacagg ctgtgccacg cgacgttcat ccgcaagtct   1320
gggacaccct acctgacaac cggcgtcact ctctcctgga cccacaacag caacacaccc   1380
accaacataa tctaccctga caagataaca caagtgccgc tggtgaaggc ttcgaacctc   1440
cattcctccg ccttcgtcct caagggtccg gcttcaccg gcggcgacat cctgggtcgc   1500
acgtcggtcg gcaacatcgc ggacattcag atgaacatta ccgcacctct gtcccagcgc   1560
tacagagtgc gtatccgcta cgcgagtacg accaacctcc aattccacac tacgatcaat   1620
gggagggcgg ttaatcaggc caacttcccg gccacgatga ccgggtcga agacctggag   1680 tacaactcgt ttcggaccat ctctttcggc acgccgttca acttcctaga cgcccagtca   1740
acctttcggc tgggagtttg gagcttcagc agcggcacag tcctcatcga ccgaatagag   1800
gtggttccga tggaggtcac gttcgaggcg gagtcggacc tggagcgagc gcagaaggct   1860
gtaaatgcgt tgttcacgag cattaaccag aagggcctca agaccgatgt cacagactac   1920
cacatcgacc aagtgtcgaa cctggtggag tgtctgtcgg atgagttctg tcttgacgag   1980
aagcgggagc tgttcgagaa ggtgaagtat gctaagcggc tgagcgacga gcggaacttg   2040
ttggctgacc cgaacttcac cagcatcaac ggacagctcg accgtgggtg gcgaggttcc   2100
accgacatca cgatacaggg cggagacgat gtgttcaagg agaactatgt gaccctctca   2160
ggaacactgg atgagtgcta cccgacctat ctctaccaga agatcgacga gagcaagctc   2220
aaggcttaca cgcgctacga actccgtggc tacatcgaag actcccagga tcttgaggtg   2280
tacctcatac gctacaacac aaaagcacgag acgctcaacg ttcctggcac cggtggtctt   2340
tggcccttgg ccgtggagag tagcatcggc gggtgcggtg agccaaaccg atgcgcgcca   2400
```

```
cagatggaat gggatccgaa cctagagtgc tcctgctcag acgaggagaa gtgcgcccac    2460
cactcccacc acttctcgct cgacattgac gttggctgca cggatctcaa cgagaaccta    2520
ggaatctggg tgatcttcaa gattaagacc cagaacggct acgccaagct cgggaatctg    2580
gagtttcttg aggagaagcc gctgatcggc gaggccctcg cgcgcgtgaa gcgagtcgag    2640
aagaagtgga agacaagcg ggagaagcta gagtttgaaa cgaacattgt ttacaacgag     2700
gcaaaggaag ccgtggacgc tctgttcgta acagtcagt acgaccgtct ccaggccgac     2760
acgaacatcg caatgataca cgcggcggat aacaaggtgc acaagattcg ggaggcttac    2820
ctgcccgagc tgtcggtcat cccaggcgta aacgctaccg tgttcgagga gctggaggaa    2880
cggatcttca ccgcgttctc cctctatgac gcaaggaacg tcatcaagaa cggcgacttc    2940
aacaacggcc tgagctgctg aacgtgaag ggccaagtgg acgtcgatca gaacgatcac     3000
cgctccgttc tggtcattcc agggtgggag tccgaggtga gccaagaggt ccatgtgtgc    3060
ccggaccgtg gctacatcct tcgggtgacc gcgtacaagg agggctacgg cgaaggctgc    3120
gtgaccatac acgagatcga caaccacacc gacgagctta agttcaagaa ctgcttcgag    3180
gaggaggtgt cactgaacaa cgccgtgacc tgcgacgagt acacgaccaa tcaggaggtc    3240
ggcggctacg ccgacgtccg ccagtcgaac aatcgaggca gcaacgaggc gtacgtgaac    3300
ccaacctcca cctcgacgga ctacgccagc tctctacgagg aggagtccta cacaaacgag    3360
cagacctaca actcgtgcga gagcaaccga ggttacggga accagatgcc gctaccgtcc    3420
gggtacgtga cgaaggagct ggagtatttc ccagagaccg acaaggtgtg gatcgagatc    3480
ggcgagacag agggcacgtt catcgtggac agcgtcgagc tgctgttgat ggaggagtga    3540
```

<210> SEQ ID NO 10
<211> LENGTH: 1179
<212> TYPE: PRT
<213> ORGANISM: Artificial
<220> FEATURE:
<223> OTHER INFORMATION: The amino acid sequence of TIC2613PL encoded by a synthetic coding sequence designed for expression in a plant cell (SEQ ID NO:9), and wherein an additional alanine amino acid is inserted immediately following the initiating methionine.

<400> SEQUENCE: 10

```
Met Ala Asp Asn Asn Ile Lys Asn Gln Cys Ile Pro Tyr Asn Cys Leu
1               5                   10                  15

Asn Asp Pro Glu Val Glu Ile Leu Gly Glu Gly Ile Thr Thr Ser
                20                  25                  30

Asn Glu Asn Leu Glu Phe Phe Leu Ser Leu Thr Lys Phe Val Leu Asn
            35                  40                  45

Arg Phe Val Pro Gly Gly Ala Tyr Val Ala Gly Leu Phe Asp Val Phe
        50                  55                  60

Trp Gly Trp Leu Lys Pro Ser Asp Trp Ser Ala Ile Leu Glu Gln Ile
65                  70                  75                  80

Glu Glu Leu Ile Asn Gln Lys Ile Glu Thr Phe Ala Arg Asn Gln Ala
                85                  90                  95

Ile Ser Arg Leu Glu Gly Leu Ser Asn Leu Tyr Glu Ile Tyr Ala Asp
            100                 105                 110

Thr Phe Lys Glu Trp Glu Lys Asp Pro Thr Asn Pro Ala Leu Arg Glu
        115                 120                 125

Glu Met Arg Thr Gln Phe Asn Asp Met Asn Ser Ser Phe Val Thr Ala
    130                 135                 140

Met Pro Leu Phe Ser Val Gln Asn Phe Glu Val Pro Leu Leu Ala Val
```

```
145                 150                 155                 160
Tyr Ala Gln Ala Ala Asn Leu His Leu Ser Val Leu Arg Asp Val Ser
                    165                 170                 175
Val Phe Gly Gln Asn Trp Gly Phe Asp Ser Ala Thr Val Asn Ser Arg
                    180                 185                 190
Tyr Asn Asp Leu Val Arg Asn Ile Arg Thr Tyr Thr Asn Tyr Val Val
                    195                 200                 205
Arg Trp Tyr Asn Thr Gly Leu Ala Arg Leu Arg Gly Thr Thr Tyr Gln
                    210                 215                 220
Asp Trp Leu Asn Tyr His Arg Phe Arg Arg Glu Leu Thr Ile Thr Ala
225                 230                 235                 240
Leu Asp Ile Ile Thr Ile Phe Pro His Tyr Asp Asn Lys Met Tyr Pro
                    245                 250                 255
Ile Gln Pro His Phe Gln Leu Thr Arg Glu Ile Tyr Thr Asp Pro Leu
                    260                 265                 270
Ile Asn Phe Asn Pro Ala Leu Gln Ser Val Ala Gln Leu Pro Leu Phe
                    275                 280                 285
Asn Glu Met Glu Asn Ser Thr Ile Arg Ser Pro His Leu Val Asp Phe
                    290                 295                 300
Leu Asn Arg Leu Thr Ile Tyr Thr Asp Trp Tyr Ser Leu Gly Arg His
305                 310                 315                 320
Tyr Tyr Trp Gly Gly His Gln Ile Val Ser Arg Gln Thr Gly Ser Thr
                    325                 330                 335
Ser Thr Ile Thr Phe Pro Ile Tyr Gly Arg Glu Ala Asn Gln Glu Ala
                    340                 345                 350
Pro Arg Thr Tyr Asn Phe Ser Gln Pro Val Phe Arg Thr Leu Ser Asn
                    355                 360                 365
Pro Thr Leu Thr Arg Leu Met Gln Pro Trp Pro Ala Pro Ala Phe Gln
                    370                 375                 380
Leu Arg Arg Leu Glu Gly Val Glu Phe Gln Thr Thr Thr Gly Asn Phe
385                 390                 395                 400
Thr Tyr Arg Gly Arg Gly Thr Val Asp Ser Phe Asp Glu Leu Pro Pro
                    405                 410                 415
Asp Asp Thr Ser Val Pro Ala Arg Glu Gly Tyr Ser His Arg Leu Cys
                    420                 425                 430
His Ala Thr Phe Ile Arg Lys Ser Gly Thr Pro Tyr Leu Thr Thr Gly
                    435                 440                 445
Val Thr Leu Ser Trp Thr His Asn Ser Asn Thr Pro Thr Asn Ile Ile
                    450                 455                 460
Tyr Pro Asp Lys Ile Thr Gln Val Pro Leu Val Lys Ala Ser Asn Leu
465                 470                 475                 480
His Ser Ser Ala Phe Val Leu Lys Gly Pro Gly Phe Thr Gly Gly Asp
                    485                 490                 495
Ile Leu Gly Arg Thr Ser Val Gly Asn Ile Ala Asp Ile Gln Met Asn
                    500                 505                 510
Ile Thr Ala Pro Leu Ser Gln Arg Tyr Arg Val Arg Ile Arg Tyr Ala
                    515                 520                 525
Ser Thr Thr Asn Leu Gln Phe His Thr Thr Ile Asn Gly Arg Ala Val
                    530                 535                 540
Asn Gln Ala Asn Phe Pro Ala Thr Met Asn Arg Val Glu Asp Leu Glu
545                 550                 555                 560
Tyr Asn Ser Phe Arg Thr Ile Ser Phe Gly Thr Pro Phe Asn Phe Leu
                    565                 570                 575
```

```
Asp Ala Gln Ser Thr Phe Arg Leu Gly Val Trp Ser Phe Ser Ser Gly
            580                 585                 590

Thr Val Leu Ile Asp Arg Ile Glu Val Val Pro Met Glu Val Thr Phe
        595                 600                 605

Glu Ala Glu Ser Asp Leu Glu Arg Ala Gln Lys Ala Val Asn Ala Leu
    610                 615                 620

Phe Thr Ser Ile Asn Gln Lys Gly Leu Lys Thr Asp Val Thr Asp Tyr
625                 630                 635                 640

His Ile Asp Gln Val Ser Asn Leu Val Glu Cys Leu Ser Asp Glu Phe
                645                 650                 655

Cys Leu Asp Glu Lys Arg Glu Leu Phe Glu Lys Val Lys Tyr Ala Lys
            660                 665                 670

Arg Leu Ser Asp Glu Arg Asn Leu Leu Ala Asp Pro Asn Phe Thr Ser
        675                 680                 685

Ile Asn Gly Gln Leu Asp Arg Gly Trp Arg Gly Ser Thr Asp Ile Thr
    690                 695                 700

Ile Gln Gly Gly Asp Asp Val Phe Lys Glu Asn Tyr Val Thr Leu Ser
705                 710                 715                 720

Gly Thr Leu Asp Glu Cys Tyr Pro Thr Tyr Leu Tyr Gln Lys Ile Asp
                725                 730                 735

Glu Ser Lys Leu Lys Ala Tyr Thr Arg Tyr Glu Leu Arg Gly Tyr Ile
            740                 745                 750

Glu Asp Ser Gln Asp Leu Glu Val Tyr Leu Ile Arg Tyr Asn Thr Lys
        755                 760                 765

His Glu Thr Leu Asn Val Pro Gly Thr Gly Leu Trp Pro Leu Ala
    770                 775                 780

Val Glu Ser Ser Ile Gly Gly Cys Gly Glu Pro Asn Arg Cys Ala Pro
785                 790                 795                 800

Gln Met Glu Trp Asp Pro Asn Leu Glu Cys Ser Cys Ser Asp Glu Glu
                805                 810                 815

Lys Cys Ala His His Ser His His Phe Ser Leu Asp Ile Asp Val Gly
            820                 825                 830

Cys Thr Asp Leu Asn Glu Asn Leu Gly Ile Trp Val Ile Phe Lys Ile
        835                 840                 845

Lys Thr Gln Asn Gly Tyr Ala Lys Leu Gly Asn Leu Glu Phe Leu Glu
    850                 855                 860

Glu Lys Pro Leu Ile Gly Glu Ala Leu Ala Arg Val Lys Arg Val Glu
865                 870                 875                 880

Lys Lys Trp Lys Asp Lys Arg Glu Lys Leu Glu Phe Glu Thr Asn Ile
                885                 890                 895

Val Tyr Asn Glu Ala Lys Glu Ala Val Asp Ala Leu Phe Val Asn Ser
            900                 905                 910

Gln Tyr Asp Arg Leu Gln Ala Asp Thr Asn Ile Ala Met Ile His Ala
        915                 920                 925

Ala Asp Asn Lys Val His Lys Ile Arg Glu Ala Tyr Leu Pro Glu Leu
    930                 935                 940

Ser Val Ile Pro Gly Val Asn Ala Thr Val Phe Glu Glu Leu Glu Gly
945                 950                 955                 960

Arg Ile Phe Thr Ala Phe Ser Leu Tyr Asp Ala Arg Asn Val Ile Lys
                965                 970                 975

Asn Gly Asp Phe Asn Asn Gly Leu Ser Cys Trp Asn Val Lys Gly Gln
            980                 985                 990
```

-continued

```
Val Asp Val Asp Gln Asn Asp His  Arg Ser Val Leu Val  Ile Pro Gly
         995             1000                 1005

Trp Glu Ser Glu Val Ser Gln  Glu Val His Val Cys  Pro Asp Arg
        1010            1015             1020

Gly Tyr Ile Leu Arg Val Thr  Ala Tyr Lys Glu Gly  Tyr Gly Glu
        1025            1030            1035

Gly Cys Val Thr Ile His Glu  Ile Asp Asn His Thr  Asp Glu Leu
        1040            1045            1050

Lys Phe Lys Asn Cys Phe Glu  Glu Glu Val Ser Leu  Asn Asn Ala
        1055            1060            1065

Val Thr Cys Asp Glu Tyr Thr  Thr Asn Gln Glu Val  Gly Gly Tyr
        1070            1075            1080

Ala Asp Val Arg Gln Ser Asn  Asn Arg Gly Ser Asn  Glu Ala Tyr
        1085            1090            1095

Val Asn Pro Thr Ser Thr Ser  Thr Asp Tyr Ala Ser  Leu Tyr Glu
        1100            1105            1110

Glu Glu Ser Tyr Thr Asn Glu  Gln Thr Tyr Asn Ser  Cys Glu Ser
        1115            1120            1125

Asn Arg Gly Tyr Gly Asn Gln  Met Pro Leu Pro Ser  Gly Tyr Val
        1130            1135            1140

Thr Lys Glu Leu Glu Tyr Phe  Pro Glu Thr Asp Lys  Val Trp Ile
        1145            1150            1155

Glu Ile Gly Glu Thr Glu Gly  Thr Phe Ile Val Asp  Ser Val Glu
        1160            1165            1170

Leu Leu Leu Met Glu Glu
        1175
```